(12) United States Patent
Crooks et al.

(10) Patent No.: US 8,703,803 B2
(45) Date of Patent: Apr. 22, 2014

(54) TRIS-QUATERNARY AMMONIUM SALTS AND METHODS FOR MODULATING NEURONAL NICOTINIC ACETYLCHOLINE RECEPTORS

(71) Applicant: University of Kentucky Research Foundation, Lexington, KY (US)

(72) Inventors: Peter A. Crooks, Little Rock, AR (US); Linda P. Dwoskin, Lexington, KY (US); Roger Papke, Gainesville, FL (US); Guangrong Zheng, Lexington, KY (US); Sangeetha Sumithran, Lexington, KY (US)

(*) Notice: Subject to any disclaimer, the term of this patent is extended or adjusted under 35 U.S.C. 154(b) by 0 days.

(21) Appl. No.: 13/624,322

(22) Filed: Sep. 21, 2012

(65) Prior Publication Data
US 2013/0030018 A1    Jan. 31, 2013

Related U.S. Application Data

(62) Division of application No. 12/158,192, filed as application No. PCT/US2006/049232 on Dec. 22, 2006, now Pat. No. 8,299,253.

(60) Provisional application No. 60/753,970, filed on Dec. 23, 2005.

(51) Int. Cl.
*A61K 31/47* (2006.01)
*A61K 31/44* (2006.01)
*A61K 31/445* (2006.01)
*A61K 31/53* (2006.01)
*A61K 31/40* (2006.01)
*A61K 31/41* (2006.01)
*A61K 31/415* (2006.01)
*C07D 217/00* (2006.01)
*C07D 213/04* (2006.01)
*C07D 401/00* (2006.01)
*C07D 215/10* (2006.01)
*C07D 215/12* (2006.01)
*A61K 31/50* (2006.01)
*A61K 31/497* (2006.01)

(52) U.S. Cl.
USPC ........... 514/358; 514/308; 514/314; 514/322; 514/333; 514/316; 514/317; 514/318; 514/241; 514/242; 514/422; 514/381; 514/383; 514/397; 514/402; 514/403; 514/406; 514/252.01; 514/252.02; 514/252.05; 546/140; 546/256; 546/255; 546/170

(58) Field of Classification Search
USPC ......... 514/358, 308, 314, 332, 336, 316, 317, 514/318, 241, 242, 422, 381, 383, 397, 402, 514/403, 406, 252.01, 252.03, 252.05, 514/252.11, 255.06, 256; 546/140, 256, 546/255, 176
See application file for complete search history.

(56) References Cited

U.S. PATENT DOCUMENTS

| 5,691,365 A | 11/1997 | Crooks et al. |
| 2003/0225142 A1 | 12/2003 | Crooks et al. |
| 2005/0261334 A1 | 11/2005 | Crooks et al. |

OTHER PUBLICATIONS

Itahara et al., "Molecular assemblies of bis- and tris-adenine derivatives," J. of Molecular Structure, 616 (2002) 213-220.*

* cited by examiner

*Primary Examiner* — Sreeni Padmanabhan
*Assistant Examiner* — Jody Karol
(74) *Attorney, Agent, or Firm* — Crowell & Moring LLP

(57) ABSTRACT

Provided are tris-quaternary ammonium compounds which are modulators of nicotinic acetylocholine receptors. Also provided are methods of using the compounds for modulating the function of a nicotinic acetylcholine receptor, and for the prevention and/or treatment of central nervous system disorders, substance use and/or abuse and or gastrointestinal tract disorders.

9 Claims, 4 Drawing Sheets

TRIS-QUATERNARY AMMONIUM SALTS AND METHODS FOR MODULATING NEURONAL NICOTINIC ACETYLCHOLINE RECEPTORS

FIELD OF THE INVENTION

The invention relates to tris-quaternary ammonium salts and their use in modulating nicotinic acetylcholine receptors.

BACKGROUND OF THE INVENTION

S(−)-nicotine (NIC) activates presynaptic and postsynaptic neuronal nicotinic receptors that evoke the release of neurotransmitters from presynaptic terminals and that modulate the depolarization state of the postsynaptic neuronal membrane, respectively. Thus, nicotine produces its effect by binding to a family of ligand-gated ion channels, stimulated by acetylcholine (ACh) or nicotine which causes the ion channel to open and cations to flux with a resulting rapid (millisecond) depolarization of the target cell. Neuronal nicotinic receptors are composed of two types of subunits, α and β, and assemble as heteromeric receptors with the general stoichiometry of 2α and 3β or as homomeric receptors with 5α subunits. Nine subtypes of the α subunit (α2 to α10) and three subtypes of the β unit (β2 to β4) are found in the central nervous system. The most common nicotinic receptor subtype in the brain is composed of two α4 and three β2 subunits, i.e., α4β2. These subunits display different, but overlapping, patterns of expression in the brain. Examples of heteromeric receptor subtypes include α4β2, α3β2, α3β4, α6β2, α4α5β2, α6α5β2, α4α6β2, α4β2β4, α3β2β4, and others. The predominant homomeric subtype includes α7, but other combinations have also been proposed.

For the most part, the actual subunit compositions and stoichiometries of nicotinic receptors in the brain remain to be elucidated. Thus, neuronal nicotinic receptor subtype diversity originates from differences in the amino acid sequence at the subunit level and from the multiple combinations of assemblies of subunits into functional receptor proteins, which affords a wide diversity of pharmacological specificity.

In spite of the extensive diversity in neuronal nicotinic receptor messenger RNA expression, only a limited number of tools are available to study the pharmacology of native receptors. Radioligands are used in many studies. [$^3$H]NIC appears to label the same sites in the brain as [$^3$H]ACh. It has been estimated that over 90% of [$^3$H]NIC binding in the brain is due to association with the heteromeric receptor that is composed of α4 and β2 subunits. Also abundant in the central nervous system are the homomeric receptors labeled by [$^3$H] methyllycaconitine (MLA), which has high affinity for the α7 nicotinic receptor subtype. Nicotinic receptor subtypes can be studied using functional assays, such as NIC-evoked neurotransmitter release (e.g., [$^3$H]dopamine (DA) release, [$^3$H] norepinephrine (NE) release, [$^3$H]serotonin (5-HT) release, [$^3$H]gamma-aminobutyric acid (GABA) release and [$^3$H] glutamate release) from superfused rat brain slices. Nicotinic receptors are located in the cell body and terminal areas of these neurotransmitter systems. NIC facilitates neurotransmitter release from nerve terminals.

The structural and functional diversity of central nervous system nicotinic receptors has stimulated a great deal of interest in developing novel, subtype-selective agonists and/or antagonists. Some of these agonists are currently being evaluated in clinical trials for cognitive enhancement and neuroprotective effects, potentially beneficial for disease states such as Alzheimer's and Parkinson's disease.

SUMMARY OF INVENTION

In one embodiment, compounds corresponding to the following structure are provided.

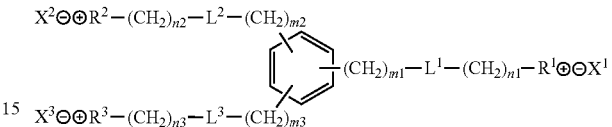

(I)

The three side chains attached to the phenyl ring may be connected to the 1, 2, and 3 positions; the 1, 2, and 4 positions; or the 1, 3 and 5 positions of the phenyl ring.

The values for m1, m2 and m3 are each independently 0, 1, 2, 3, 4 or 5.

The values for n1, n2, and n3 are each independently 1, 2, 3, 4 or 5.

$X^{1\ominus}$, $X^{2\ominus}$, and $X^{3\ominus}$ are each independently an organic or inorganic anion.

$L^1$, $L^2$ and $L^3$ are each independently chosen from the group consisting of —CH$_2$—CH$_2$—, cis —CH=CH—, trans —CH=CH—, —C≡C—, —CH$_2$—S—, —S—CH$_2$—, —Se—CH$_2$—, —CH$_2$—Se—, —CH$_2$—O—, —O—CH$_2$—, —CH$_2$—NH—, —NH—CH$_2$—, —CH$_2$—NR— where R is a branched or straight chain alkyl group of one to four carbons, —NR—CH$_2$— where R is a branched or straight chain alkyl group of one to four carbons, —CH=N—, —N=CH—, and —N=N—.

$R^1$, $R^2$, and $R^3$ are each independently five or six membered nitrogen containing rings as shown in formulas (IIA) and (IIB).

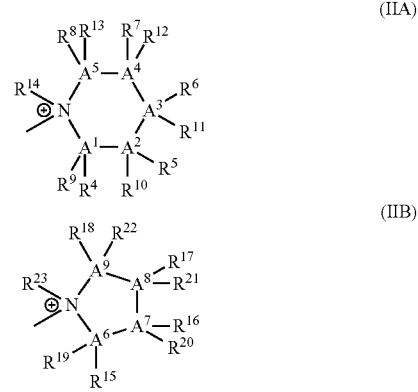

$A^1$ is carbon or nitrogen, provided that when $A^1$ joins a ring atom with an unsaturated bond or is a nitrogen, $R^9$ is absent, and when $A^1$ joins a ring atom an unsaturated bond and is a nitrogen, both $R^4$ and $R^9$ are absent.

$A^2$ is carbon or nitrogen, provided that when $A^2$ joins a ring atom an unsaturated bond or is a nitrogen, $R^{10}$ is absent, and when $A^2$ joins a ring atom an unsaturated bond and is a nitrogen, both $R^5$ and $R^{10}$ are absent.

$A^3$ is carbon or nitrogen, provided that when $A^3$ joins a ring atom an unsaturated bond or is a nitrogen, $R^{11}$ is absent, and when $A^3$ joins a ring atom an unsaturated bond and is a nitrogen, both $R^6$ and $R^{11}$ are absent.

$A^4$ is carbon or nitrogen; provided that when $A^4$ joins a ring atom an unsaturated bond or is a nitrogen, $R^{12}$ is absent, and when $A^4$ joins a ring atom an unsaturated bond and is a nitrogen, both $R^7$ and $R^{12}$ are absent.

$A^5$ is carbon or nitrogen, provided that when $A^5$ joins a ring atom an unsaturated bond or is a nitrogen, $R^{13}$ is absent, and when $A^5$ joins a ring atom an unsaturated bond and is a nitrogen, both $R^8$ and $R^{13}$ are absent.

$A^6$ is carbon or nitrogen, provided that when $A^6$ joins a ring atom an unsaturated bond or is a nitrogen, $R^{19}$ is absent, and when $A^6$ joins a ring atom an unsaturated bond and is a nitrogen, both $R^{15}$ and $R^{19}$ are absent.

$A^7$ is carbon or nitrogen, provided that when $A^7$ joins a ring atom an unsaturated bond or is a nitrogen, $R^{20}$ is absent, and when $A^7$ joins a ring atom an unsaturated bond and is a nitrogen, both $R^{16}$ and $R^{20}$ are absent.

$A^8$ is carbon or nitrogen, provided that when $A^8$ joins a ring atom an unsaturated bond or is a nitrogen, $R^{21}$ is absent, and when $A^8$ joins a ring atom an unsaturated bond and is a nitrogen, both $R^{17}$ and $R^{21}$ are absent.

$A^9$ is carbon or nitrogen, provided that when $A^9$ joins a ring atom an unsaturated bond or is a nitrogen, $R^{22}$ is absent, and when $A^9$ joins a ring atom an unsaturated bond and is a nitrogen, both $R^{18}$ and $R^{22}$ are absent.

$R^{14}$ or $R^{23}$ is absent when any of the bonds to the ammonium nitrogen is unsaturated, and $R^{14}$ or $R^{23}$ is a straight chain or branched alkyl group of four carbons or fewer when all of the bonds to the ammonium nitrogen are saturated.

$R^4, R^5, R^6, R^7, R^8, R^9, R^{10}, R^{11}, R^{12}$, and $R^{13}$ or $R^{15}, R^{16}, R^{17}, R^{18}, R^{19}, R^{20}, R^{21}$, and $R^{22}$, when present, are each independently selected from hydrogen; alkyl; substituted alkyl; cycloalkyl; substituted cycloalkyl; alkenyl; substituted alkenyl; alkynyl; substituted alkynyl; aryl; substituted aryl; alkylaryl; substituted alkylaryl; arylalkyl; substituted arylalkyl; arylalkenyl; substituted arylalkenyl; arylalkynyl; substituted arylalkynyl; heterocyclic; substituted heterocyclic; halo; cyano; nitro; $SOY^1$, $SO_2Y^1$, $SO_2OY^1$ or $SO_2NHY^1$, where $Y^1$ is selected from hydrogen, lower alkyl, alkenyl, alkynyl or aryl, and where $Y^1$ is not hydrogen in $SOY^1$ and if $Y^1$ is alkenyl or alkynyl, the site of unsaturation is not conjugated with a heteroatom; $COY^2$, where $Y^2$ is selected from hydrogen, alkyl, substituted alkyl, cycloalkyl, substituted cycloalkyl, alkoxy, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, heterocyclic, or substituted heterocyclic, and where if $Y^2$ comprises alkenyl or alkynyl, the site of unsaturation is not conjugated with the carbonyl group; $OY^3$, where $Y^3$ is selected from hydrogen, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, acyl, substituted acyl, alkylsulfonyl, arylsulfonyl, heterocyclic, or substituted heterocyclic, where if $Y^3$ comprises alkenyl or alkynyl, the site of unsaturation is not conjugated with the oxygen; $NY^4Y^5$, where $Y^4$ and $Y^5$ are each independently selected from hydrogen, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, acyl, substituted acyl, alkylsulfonyl, arylsulfonyl, heterocyclic, or substituted heterocyclic, where if $Y^4$ or $Y^5$ comprises alkenyl or alkynyl, the site of unsaturation is not conjugated with the nitrogen; $SY^6$, where $Y^6$ is selected from hydrogen, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, heterocyclic, or substituted heterocyclic, and where if $Y^6$ comprises alkenyl or alkynyl, the site of unsaturation is not conjugated with the sulfur; or $R^4$ and $R^5$ together with $A^1$ and $A^2$, or $R^5$ and $R^6$ together with $A^2$ and $A^3$, or $R^{15}$ and $R^{16}$ together with $A^6$ and $A^7$, or $R^{16}$ and $R^{17}$ together with $A^7$ and $A^8$ independently form a three to eight member cyclolkane, substituted cycloalkane, cycloalkene, substituted cycloalkene, aryl, substituted aryl, heterocycle with one to three hetero atoms in the ring, or substituted heterocycle with one to three hetero atoms in the ring.

In another embodiment, a composition is provided comprising a pharmaceutically acceptable carrier and a compound as described above.

In another embodiment, a method is provided for selectively modulating the function of a nicotinic acetylcholine receptor comprising administering a therapeutically effective amount of a compound as described above to a mammalian subject in need thereof.

In another embodiment, a method is provided for preventing and/or treating a central nervous system associated disorder comprising administering a therapeutically effective amount of a compound as described above to a mammalian subject in need thereof.

In another embodiment, a method is provided for preventing and/or treating substance use and/or abuse comprising administering a therapeutically effective amount of a compound as described above to a mammalian subject in need thereof.

In another embodiment, a method is provided for preventing and/or treating gastrointestinal tract disorders comprising administering a therapeutically effective amount of a compound as described above to a mammalian subject in need thereof.

Other methods, features and advantages of the present invention will be or become apparent to one with skill in the art upon examination of the following detailed descriptions. It is intended that all such additional methods, features and advantages be included within this description, be within the scope of the present invention, and be protected by the accompanying claims.

DETAILED DESCRIPTION OF INVENTION

Figure 1:
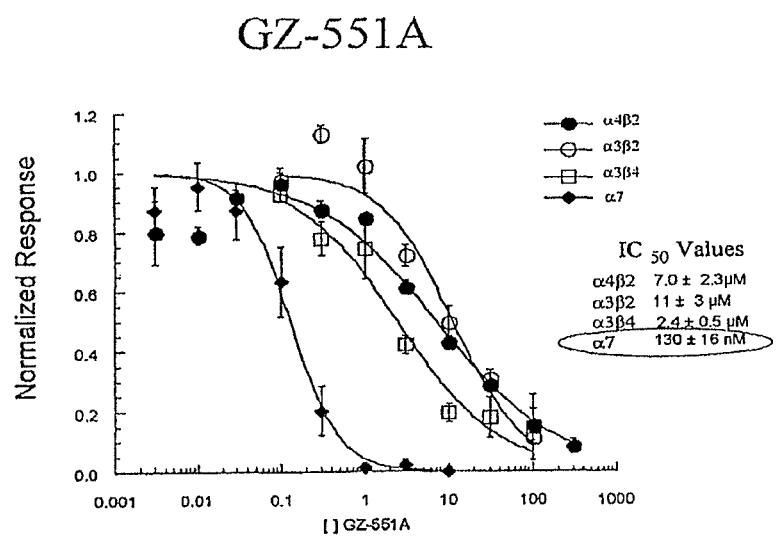
FIG. 1 shows concentration-response curves for GZ551A in each four subtypes of nicotinic receptor ($\alpha 4\beta 2$, $\alpha 3\beta 2$, $\alpha 3\beta 4$ and $\alpha 7$) expressed in *Xenopus* oocytes.

Before the present compositions and methods are described, it is to be understood that the invention is not limited to the particular methodologies, protocols, assays, and reagents described, as these may vary. It is also to be understood that the terminology used herein is intended to describe particular embodiments of the present invention, and is in no way intended to limit the scope of the present invention as set forth in the appended claims.

It must be noted that as used herein and in the appended claims, the singular forms "a," "an," and "the" include plural references unless the context clearly dictates otherwise.

Unless defined otherwise, all technical and scientific terms used herein have the same meanings as commonly understood by one of ordinary skill in the art to which this invention belongs. All publications cited herein are incorporated herein by reference in their entirety for the purpose of describing and disclosing the methodologies, reagents, and tools reported in the publications that might be used in connection with the invention. Nothing herein is to be construed as an admission that the invention is not entitled to antedate such disclosure by virtue of prior invention.

The term "nicotinic acetylcholine receptor" refers to the endogenous acetylcholine receptor having binding sites for acetylcholine which also bind to nicotine. The term "nicotinic acetylcholine receptor" includes the term "neuronal nicotinic acetylcholine receptor."

The terms "subtype of nicotinic acetylcholine receptor," and "nicotinic acetylcholine receptor subtype" refer to various subunit combinations of the nicotinic acetylcholine receptor, and may refer to a particular homomeric or heteromeric complex, or multiple homomeric or heteromeric complexes.

The term "agonist" refers to a substance which interacts with a receptor and increases or prolongs a physiological response (i.e. activates the receptor).

The term "partial agonist" refers to a substance which interacts with and activates a receptor to a lesser degree than an agonist.

The term "antagonist" refers to a substance which interacts with and decreases the extent or duration of a physiological response of that receptor.

The terms "disorder," "disease," and "condition" are used inclusively and refer to any status deviating from normal.

The term "central nervous system associated disorders" includes any cognitive, neurological, and mental disorders causing aberrant or pathological neural signal transmission, such as disorders associated with the alteration of normal neurotransmitter release in the brain.

The term "lower alkyl" refers to straight or branched chain alkyl radicals having in the range of 1 to 4 carbon atoms.

The term "alkyl" refers to straight or branched chain alkyl radicals having 1 to 19 carbon atoms, and "substituted alkyl" refers to alkyl radicals further bearing one or more substituents including, but not limited to, hydroxy, alkoxy (of a lower alkyl group), mercapto (of a lower alkyl group), aryl, heterocyclic, halogen, trifluoromethyl, cyano, nitro, amino, carboxyl, carbamate, sulfonyl, and sulfonamide.

The term "cycloalkyl" refers to cyclic ring-containing moieties containing 3 to 8 carbon atoms, and "substituted cycloalkyl" refers to cycloalkyl moieties further bearing one or more substituents as set forth above.

The term "alkenyl" refers to straight or branched chain hydrocarbyl groups having at least one carbon-carbon double bond and having 2 to 19 carbon atoms, and "substituted alkenyl" refers to alkenyl groups further bearing one or more substituents as set forth above.

The term "alkynyl" refers to straight or branched chain hydrocarbyl moieties having at least one carbon-carbon triple bond and having 2 to 19 carbon atoms, and "substituted alkynyl" refers to alkynyl moieties further bearing one or more substituents as set forth above.

The term "aryl" refers to aromatic groups having 6 to 24 carbon atoms, and "substituted aryl" refers to aryl groups further bearing one or more substituents as set forth above.

The term "alkylaryl" refers to alkyl-substituted aryl groups, and "substituted alkylaryl" refers to alkylaryl groups further bearing one or more substituents as set forth above.

The term "arylalkyl" refers to aryl-substituted alkyl groups, and "substituted arylalkyl" refers to arylalkyl groups further bearing one or more substituents as set forth above.

The term "arylalkenyl" refers to aryl-substituted alkenyl groups, and "substituted arylalkenyl" refers to arylalkenyl groups further bearing one or more substituents as set forth above.

The term "arylalkynyl" refers to aryl-substituted alkynyl groups, and "substituted arylalkynyl" refers to arylalkynyl groups further bearing one or more substituents as set forth above.

The term "heterocyclic" refers to cyclic moieties containing one or more heteroatoms as part of the ring structure and having 3 to 24 carbon atoms, and "substituted heterocyclic" refers to heterocyclic moieties further bearing one or more substituents as set forth above.

The term "acyl" refers to alkyl-carbonyl groups, and "substituted acyl" refers to acyl groups further bearing one or more substituents as set forth above.

The term "halogen" refers to fluoride, chloride, bromide or iodide groups.

It is understood that in all substituted groups defined above, polymers arrived at by defining substituents with further substituents to themselves (e.g. substituted aryl having a substituted aryl group as a substituent which is itself substituted with a substituted aryl group, etc.) are not intended for inclusion herein. In such cases, the maximum number of such substituents is three. That is to say that each of the above definitions is constrained by a limitation that, for example, substituted aryl groups are limited to -substituted aryl-(substituted aryl)-substituted aryl.

Compounds of the present invention are tris-quaternary ammonium salts corresponding to Formula (I):

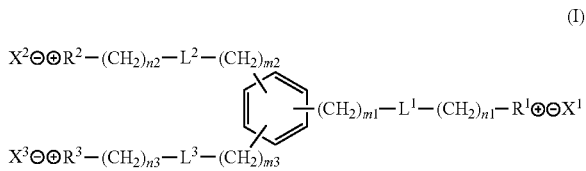

(I)

The three side chains attached to the phenyl ring may be connected to the 1, 2, and 3 positions; the 1, 2, and 4 positions; or the 1, 3 and 5 positions of the phenyl ring.

The values for m1, m2 and m3 are each independently 0, 1, 2, 3, 4 or 5.

The values for n1, n2, and n3 are each independently 1, 2, 3, 4 or 5.

$X^{1\ominus}$, $X^{2\ominus}$ and $X^{3\ominus}$ are each independently an organic or inorganic anion.

$L^1$, $L^2$ and $L^3$ are each independently chosen from the group consisting of —$CH_2$—$CH_2$—, cis —CH=CH—, trans —CH=CH—, —C≡C—, —$CH_2$—S—, —S—$CH_2$—, —Se—$CH_2$—, —$CH_2$—Se—, —$CH_2$—O—, —O—$CH_2$—, —$CH_2$—NH—, —NH—$CH_2$—, —$CH_2$—NR— where R is a branched or straight chain alkyl group of one to four carbons, —NR—$CH_2$— where R is a branched or straight chain alkyl group of one to four carbons, —CH=N—, —N=CH—, and —=N—.

$R^1$, $R^2$, and $R^3$ are each independently five or six membered nitrogen containing rings as shown in formulas (IIA) and (IIB).

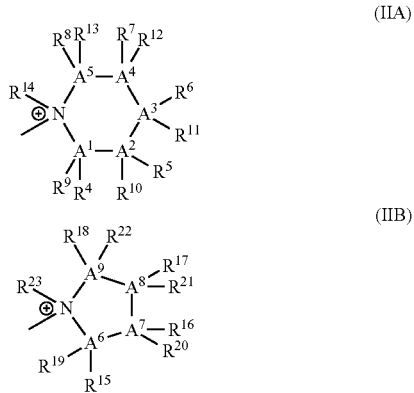

$A^1$ is carbon or nitrogen, provided that when $A^1$ joins a ring atom with an unsaturated bond or is a nitrogen, $R^9$ is absent, and when $A^1$ joins a ring atom with an unsaturated bond and is a nitrogen, both $R^4$ and $R^9$ are absent.

$A^2$ is carbon or nitrogen, provided that when $A^2$ joins a ring atom with an unsaturated bond or is a nitrogen, $R^{10}$ is absent, and when $A^2$ joins a ring atom with an unsaturated bond and is a nitrogen, both $R^5$ and $R^{10}$ are absent.

$A^3$ is carbon or nitrogen, provided that when $A^3$ joins a ring atom with an unsaturated bond or is a nitrogen, $R^{11}$ is absent, and when $A^3$ joins a ring atom with an unsaturated bond and is a nitrogen, both $R^6$ and $R^{11}$ are absent.

$A^4$ is carbon or nitrogen, provided that when $A^4$ joins a ring atom with an unsaturated bond or is a nitrogen, $R^{12}$ is absent, and when $A^4$ joins a ring atom with an unsaturated bond and is a nitrogen, both $R^7$ and $R^{12}$ are absent.

$A^5$ is carbon or nitrogen, provided that when $A^5$ joins a ring atom with an unsaturated bond or is a nitrogen, $R^{13}$ is absent, and when $A^5$ joins a ring atom with an unsaturated bond and is a nitrogen, both $R^8$ and $R^{13}$ are absent.

$A^6$ is carbon or nitrogen, provided that when $A^6$ joins a ring atom with an unsaturated bond or is a nitrogen, $R^{19}$ is absent, and when $A^6$ joins a ring atom with an unsaturated bond and is a nitrogen, both $R^{15}$ and $R^{19}$ are absent.

$A^7$ is carbon or nitrogen, provided that when $A^7$ joins a ring atom with an unsaturated bond or is a nitrogen, $R^{20}$ is absent, and when $A^7$ joins a ring atom with an unsaturated bond and is a nitrogen, both $R^{16}$ and $R^{20}$ are absent.

$A^8$ is carbon or nitrogen, provided that when $A^8$ joins a ring atom with an unsaturated bond or is a nitrogen, $R^{21}$ is absent, and when $A^8$ joins a ring atom with an unsaturated bond and is a nitrogen, both $R^{17}$ and $R^{21}$ are absent.

$A^9$ is carbon or nitrogen, provided that when $A^9$ joins a ring atom with an unsaturated bond or is a nitrogen, $R^{22}$ is absent, and when $A^9$ joins a ring atom with an unsaturated bond and is a nitrogen, both $R^{18}$ and $R^{22}$ are absent.

$R^{14}$ or $R^{23}$ is absent when any of the bonds to the ammonium nitrogen is unsaturated, and $R^{14}$ or $R^{23}$ is a straight chain or branched alkyl group of four carbons or fewer when all of the bonds to the ammonium nitrogen are saturated.

$R^4$, $R^5$, $R^6$, $R^7$, $R^8$, $R^9$, $R^{10}$, $R^{11}$, $R^{12}$, and $R^{13}$ or $R^{15}$, $R^{16}$, $R^{17}$, $R^{18}$, $R^{19}$, $R^{20}$, $R^{21}$, and $R^{22}$, when present, are each independently selected from hydrogen, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, heterocyclic, substituted heterocyclic, halo, cyano, nitro, $SOY^1$, $SO_2Y^1$, $SO_2OY^1$ or $SO_2NHY^1$, where $Y^1$ is selected from hydrogen, lower alkyl, alkenyl, alkynyl or aryl, and where $Y^1$ is not hydrogen in $SOY^1$ and if $Y^1$ is alkenyl or alkynyl, the site of unsaturation is not conjugated with a heteroatom; $COY^2$, where $Y^2$ is selected from hydrogen, alkyl, substituted alkyl, cycloalkyl, substituted cycloalkyl, alkoxy, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, heterocyclic, or substituted heterocyclic, and where if $Y^2$ comprises alkenyl or alkynyl, the site of unsaturation is not conjugated with the carbonyl group; $OY^3$, where $Y^3$ is selected from hydrogen, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, acyl, substituted acyl, alkylsulfonyl, arylsulfonyl, heterocyclic, or substituted heterocyclic, where if $Y^3$ comprises alkenyl or alkynyl, the site of unsaturation is not conjugated with the oxygen; $NY^4Y^5$, where $Y^4$ and $Y^5$ are each independently selected from hydrogen, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, acyl, substituted acyl, alkylsulfonyl, arylsulfonyl, heterocyclic, or substituted heterocyclic, where if $Y^4$ or $Y^5$ comprises alkenyl or alkynyl, the site of unsaturation is not conjugated with the nitrogen; $SY^6$, where $Y^6$ is selected from hydrogen, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, heterocyclic, or substituted heterocyclic, and where if $Y^6$ comprises alkenyl or alkynyl, the site of unsaturation is not conjugated with the sulfur; or $R^4$ and $R^5$ together with $A^1$ and $A^2$, or $R^5$ and $R^6$ together with $A^2$ and $A^3$, or $R^{15}$ and $R^{16}$ together with $A^6$ and $A^7$, or $R^{16}$ and $R^{17}$ together with $A^7$ and $A^8$ independently form a three to eight member cyclolkane, substituted cycloalkane, cycloalkene, substituted cycloalkene, aryl, substituted aryl, heterocycle with one to three hetero atoms in the ring, or substituted heterocycle with one to three hetero atoms in the ring.

For example, $R^1$, $R^2$, and $R^3$ include pyrrole, pyrrolidine, pyrazole, imidazole, 1,2,3-triazole, 1,2,4-triazole, pyridine, piperidine, quinoline, tetrahydroquinoline, isoquinoline, tetrahydroisoquinoline, pyrazine, piperazine, pyridazine, and triazine.

As another example, $R^4$, $R^5$, $R^6$, $R^7$, $R^8$, $R^9$, $R^{10}$, $R^{11}$, $R^{12}$, $R^{13}$, $R^{15}$, $R^{16}$, $R^{17}$, $R^{18}$, $R^{19}$, $R^{20}$, $R^{21}$, and $R^{22}$, include hydrogen, methyl, ethyl, propyl, butyl, trifluoromethyl, pyrrolidine, N-alkyl pyrrolidine (for example where the alkyl chain is methyl, ethyl or propyl), unsaturated pyrrolidine, unsaturated N-alkyl pyrrolidine (for example where the alkyl chain is methyl, ethyl or propyl), aziridine, N-methyl aziridine, azetidine, N-methyl azetidine, unsaturated azetidine, unsaturated N-methyl azetidine, piperidine, N-methyl piperidine, unsaturated piperidine, unsaturated N-methyl piperidine, azepane, N-methyl azepane, unsaturated azepane, unsaturated N-methyl azepane, azocane, N-methyl azocane, unsaturated azocane, unsaturated N-methyl azocane, 1-aza-bicyclo[3.2.1]octane, 1-aza-bicyclo[2.2.1]heptane, 8-methyl-8-aza-bicyclo [3.2.1]octane, 1-aza-tricyclo[3.3.1.1$^{3,7}$] decane, methyl cycloalkyl, methyl substituted cycloalkyl, methylpyrrolidine, methyl N-alkyl pyrrolidine (for example where the alkyl chain is methyl, ethyl or propyl), methyl unsaturated pyrrolidine, methyl unsaturated N-alkyl pyrrolidine (for example where the alkyl chain is methyl, ethyl or propyl), methyl aziridine, methyl N-methyl aziridine, methyl azetidine, methyl N-methyl azetidine, methyl unsaturated azetidine, methyl unsaturated N-methyl azetidine, methyl piperidine, methyl N-methyl piperidine, methyl unsaturated piperidine, methyl unsaturated N-methyl piperidine, methyl azepane, methyl N-methyl azepane, methyl unsaturated azepane, methyl unsaturated N-methyl azepane, methyl azocane, methyl N-methyl azocane, methyl unsaturated azocane, methyl unsaturated N-methyl azocane, methyl-1-aza-bicyclo [3.2.1]octane, methyl-1-aza-bicyclo[2.2.1]heptane, 8-methyl-8-aza-bicyclo[3.2.1]octane, and methyl-1-aza-tricyclo [3.3.1.1$^{3,7}$]decane.

As a further example, when $R^4$ and $R^5$ together with $A^1$ and $A^2$, or $R^5$ and $R^6$ together with $A^2$ and $A^3$, or $R^{15}$ and $R^{16}$ together with $A^6$ and $A^7$, or $R^{16}$ and $R^{17}$ together with $A^7$ and $A^8$ independently form a three to eight-membered ring, that ring may be a heterocycle containing up to three hetero atoms (for example nitrogen, oxygen or sulfur) in the ring, and further may be substituted with one or more substituents. For example, possible rings include benzene, pyridine, pyran, indene, isoindene, benzofuran, isobenzofuran, benzo[b]thiophene, benzo[c]thiophene, indole, indolenine, isoindole, cyclopental[b]pyridine, pyrano[3,4-b]pynrole, indazole, indoxazine, benzoxazole, anthranil naphthalene, tetralin, decalin, chromene, coumarin, chroman-4-one, isocoumarin, isochromen-3-one, quinoline, isoquinoline, cinnoline, quinazoline, naphthyrdine, pyrido[3,4-b]-pyridine, pyridol [3,2-b]pyridine, pyrido[4,3,-b]-pyridine, benzoxazine, anthracene, phenanthrene, phenalene, fluorene, carazole, xanthene, acnidine, octahydro-[1]pyridine, 1-methyloctahydro-[1]pyridine, octahydroindole, 1-methyloctahydro-indole, octahydro-cyclopenta[b]pyrrole, 1-methyloctahydro-cyclopenta[b]pyrrole, decahydroquinoline, and 1-methyldecahydroquinoline.

$X^{1\ominus}$, $X^{2\ominus}$, and $X^{3\ominus}$, for example, include F⁻, Cl⁻, Br⁻, I⁻, NO$_2^-$, HSO$_4^-$, SO$_4^-$, HPO$_4^-$, PO$_4^{2-}$, methanesulfonate, trifluoromethane sulfate, p-toluenesulfonate, benzenesulfonate, salicylate, proprionate, ascorbate, aspartate, fumarate, galactarate, maleate, citrate, glutamate, glycolate, lactate, malate, maleate, tartrate, oxalate, succinate, or similar pharmaceutically acceptable organic acid addition salts, including the pharmaceutically acceptable salts listed in the Journal of Pharmaceutical Sciences volume 66, page 2, 1977, which are hereby incorporated by reference. The above salt forms may be in some cases hydrates or solvates with alcohols and other solvents.

In a compound of Formula (I), preferably the phenyl ring is substituted at the 1, 3 and 5 positions.

In a compound of Formula (I), preferably $A^1$, $A^2$, $A^3$, $A^4$, and $A^5$ are carbon. In a compound of Formula (I), preferably $R^1$, $R^2$, and $R^3$ are substituted, six-membered, aromatic rings. More preferably, $R^1$, $R^2$, and $R^3$ are substituted pyridinium rings.

In a compound of Formula (I), preferably $R^4$ is hydrogen, alkyl, or forms an aryl ring with $A^1$, $A^2$ and $R^5$. More preferably, $R^4$ is hydrogen, methyl or forms a phenyl group with $A^1$, $A^2$ and $R^5$.

In a compound of Formula (I), preferably $R^5$ is hydrogen, alkyl, phenyl, 1-methyl-2-pyrrolidinyl, forms a six-membered ring with $A^1$, $A^2$ and $R^4$, or forms an aryl ring with $A^2$, $A^3$ and $R^6$. More preferably, $R^5$ is hydrogen, methyl, butyl, phenyl, 1-methyl-2-pyrrolidinyl, forms a phenyl group with $A^1$, $A^2$ and $R^4$, or forms a phenyl group with $A^2$, $A^3$ and $R^6$.

In a compound of Formula (I), preferably $R^6$ is hydrogen, alkyl, or forms an aryl ring with $A^2$, $A^3$ and $R^5$. More preferably, $R^6$ is hydrogen, methyl or forms a phenyl group with $A^2$, $A^3$ and $R^5$.

In a compound of Formula (I), preferably $R^7$ is hydrogen or alkyl. More preferably, $R^7$ is hydrogen or methyl.

In a compound of Formula (I), preferably $R^5$ is hydrogen.

In a compound of Formula (I), preferably m=0.

In a compound of Formula (I), preferably n=3.

In a compound of Formula (I), preferably $L^1$, $L^2$ and $L^3$ are —CH$_2$—CH$_2$— or —C≡C—.

In a compound of Formula (I), preferably $X^{1\ominus}$, $X^{2\ominus}$, and $X^{3\ominus}$ are halogens. More preferably, $X^{1\ominus}$, $X^{2\ominus}$, and $X^{3\ominus}$ are bromide.

In one embodiment, the compound of Formula (I) is defined wherein the phenyl ring is 1,3,5 substituted; wherein m=0; wherein n=3; wherein L is —CH$_2$CH$_2$— or —C≡C—; wherein $R^1$, $R^2$, and $R^3$ are pyridinium rings; wherein $R^4$ is hydrogen, methyl or forms a phenyl group with $A^1$, $A^2$ and $R^5$; wherein $R^5$ is hydrogen, methyl, phenyl, butyl, 1-methyl-2-pyrrolidinyl, forms a phenyl group with $A^1$, $A^2$ and $R^4$, or forms a phenyl group with $A^2$, $A^3$ and $R^6$; wherein $R^6$ is hydrogen, methyl or forms a phenyl group with $A^2$, $A^3$ and $R^5$; and wherein $X^1$, $X^2$, and $X^3$ are Br.

In another embodiment, the compound of Formula (I) is defined wherein the phenyl ring is 1,3,5 substituted; wherein m=0; wherein n=3; wherein L is —CH$_2$CH$_2$—; wherein $R^1$, $R^2$, and $R^3$ are pyridinium rings; wherein $R^4$ is hydrogen, methyl or forms a phenyl group with $A^1$, $A^2$ and $R^5$; wherein $R^5$ is hydrogen, methyl, phenyl, butyl, 1-methyl-2-pyrrolidinyl, forms a phenyl group with $A^1$, $A^2$ and $R^4$, or forms a phenyl group with $A^2$, $A^3$ and $R^6$; wherein $R^6$ is hydrogen, methyl or forms a phenyl group with $A^2$, $A^3$ and $R^5$; and wherein $X^1$, $X^2$, and $X^3$ are Br.

In another embodiment, the compound of Formula (I) is defined wherein the phenyl ring is 1,3,5 substituted; wherein in =0; wherein n=3; wherein L is —C≡C—; wherein $R^1$, $R^2$, and $R^3$ are pyridinium rings; wherein $R^4$ is hydrogen, methyl or forms a phenyl group with $A^1$, $A^2$ and $R^5$; wherein $R^5$ is hydrogen, methyl, phenyl, butyl, 1-methyl-2-pyrrolidinyl, forms a phenyl group with $A^1$, $A^2$ and $R^4$, or forms a phenyl group with $A^2$, $A^3$ and $R^6$; wherein $R^6$ is hydrogen, methyl or forms a phenyl group with $A^2$, $A^3$ and $R^5$; and wherein $X^1$, $X^2$, and $X^3$ are Br.

Exemplary compounds for this application are presented in Table 1.

TABLE 1

[Structure: 1,3,5-trisubstituted benzene with three linkers L connecting to pyridinium rings bearing R4, R5, R6, R7 substituents; 3 Br− counterions]

| ID # | R4 | R5 | R6 | R7 | L |
|---|---|---|---|---|---|
| GZ550A | hydrogen | methyl | hydrogen | hydrogen | —C≡C— |
| GZ550B | hydrogen | phenyl | hydrogen | hydrogen | —C≡C— |
| GZ551A | hydrogen | butyl | hydrogen | hydrogen | —C≡C— |
| GZ551B | hydrogen | 1-methyl-2-pyrrolidinyl | hydrogen | hydrogen | —C≡C— |
| GZ552A | phenyl with $R^5$ | phenyl with $R^4$ | hydrogen | hydrogen | —C≡C— |
| GZ552B | hydrogen | phenyl with $R^6$ | phenyl with $R^5$ | hydrogen | —C≡C— |
| GZ553A | hydrogen | methyl | hydrogen | methyl | —C≡C— |
| GZ553B | hydrogen | methyl | methyl | hydrogen | —C≡C— |
| GZ554A | methyl | hydrogen | hydrogen | hydrogen | —C≡C— |
| GZ554B | hydrogen | hydrogen | methyl | hydrogen | —C≡C— |
| GZ555A | hydrogen | methyl | hydrogen | hydrogen | —CH$_2$CH$_2$— |
| GZ555B | methyl | hydrogen | hydrogen | hydrogen | —CH$_2$CH$_2$— |
| GZ555C | hydrogen | hydrogen | methyl | hydrogen | —CH$_2$CH$_2$— |
| GZ556A | phenyl with $R^5$ | phenyl with $R^4$ | hydrogen | hydrogen | —CH$_2$CH$_2$— |
| GZ556B | hydrogen | phenyl with $R^6$ | phenyl with $R^5$ | hydrogen | —CH$_2$CH$_2$— |
| GZ557A | hydrogen | methyl | hydrogen | methyl | —CH$_2$CH$_2$— |
| GZ557B | hydrogen | methyl | methyl | hydrogen | —CH$_2$CH$_2$— |
| GZ558A | hydrogen | phenyl | hydrogen | hydrogen | —CH$_2$CH$_2$— |
| GZ558B | hydrogen | butyl | hydrogen | hydrogen | —CH$_2$CH$_2$— |
| GZ558C | hydrogen | 1-methyl-2-pyrrolidinyl | hydrogen | hydrogen | —CH$_2$CH$_2$— |

Exemplary compounds of the present invention include: 1,3,5-tris-[5-(2-picolinium)-pent-1-ynyl]-benzene tribromide; 1,3,5-tris-[5-(3-picolinium)-pent-1-ynyl]-benzene tribromide; 1,3,5-tris-[5-(4-picolinium)-pent-1-ynyl]-benzene tribromide; 1,3,5-tris-[5-(3-butyl-pyridinium)-pent-1-ynyl]-benzene tribromide; 1,3,5-tris-[5-(3-phenyl-pyridinium)-pent-1-ynyl]-benzene tribromide; 1,3,5-tris-{5-[3-(1-methyl-2-S-pyrrolidinyl)pyridinium]-pent-1-ynyl}-benzene tribromide; 1,3,5-tris-[5-(1-quinolinium)-pent-1-ynyl]-benzene tribromide; 1,3,5-tris-[5-(2-isoquinolinium)-pent-1-ynyl]-benzene tribromide; 1,3,5-tris-[5-(3,5-lutidinium)-pent-1-ynyl]-benzene tribromide; 1,3,5-tris-[5-(3,4-lutidinium)-pent-1-ynyl]-benzene tribromide; 1,3,5-tris-[5-(2-picolinium)-pentyl]-benzene tribromide; 1,3,5-tris-[5-(3-picolinium)-pentyl]benzene tribromide; 1,3,5-tris-[5-(4-picolinium)-pentyl]-benzene tribromide; 1,3,5-tris-[5-(3-butyl-pyridinium)-pentyl]-benzene tribromide; 1,3,5-tris-[5-(3-phenyl-pyridinium)-pentyl]benzene tribromide; 1,3,5-tris-{5-[3-(1-methyl-2-S-pyrrolidinyl)pyridinium]-pentyl}-benzene tribromide; 1,3,5-tris-[5-(1-quinolinium)-pentyl]-benzene tribromide; 1,3,5-tris-[5-(2-isoquinolinium)-pentyl]-benzene tribromide; 1,3,5-tris-[5-(3,5-lutidinium)-pentyl]-benzene tribromide; and 1,3,5-tris-[5-(3,4-lutidinium)-pentyl]-benzene tribromide.

The compounds of the present invention may contain one or more stereocenters. The invention includes all possible diastereomers and all enantiomeric forms as well as racemic mixtures. The compounds can be separated into substantially optically pure compounds.

The compounds of the invention are nicotinic acetylcholine receptor agents. Thus, they may augment or inhibit [$^3$H]nicotine binding, [$^3$H]MLA binding, evoke or inhibit neurotransmitter release, and/or evoke or inhibit the flux of ions through the nicotinic receptor. Moreover, the compounds of the invention may act either at presynaptic sites or postsynaptic sites, for example, at a postsynaptic acetylcholine receptor containing an α7 subunit. When acting at a postsynaptic site, neurotransmitter release per se is not altered. Rather, the compounds of the invention may act by interacting with a postsynaptic acetylcholine receptor to change the membrane potential of the cell, thereby increasing or decreasing the likelihood of firing an action potential. Alternatively, interaction of a compound of the invention with a postsynaptic acetylcholine receptor may result in the alteration of one or more second messenger systems within the cell so as to decrease or increase the nicotinic cholinergic response.

In one embodiment, the present invention relates to a method for selectively modulating the function of a nicotinic acetylcholine receptor comprising administering to a mammalian subject in need thereof a therapeutically effective amount of a compound of Formula (I). In such a method, the compound of Formula (I) may selectively bind to one or more subtypes of nicotinic acetylcholine receptor. The compound of Formula (I) may act as an agoinst or partial agonist of nicotinic acetylcholine receptor function. Hence the compound of Formula (I) may increase or prolong the release of a neurotransmitter from a central nervous system tissue. The neurotransmitter affected may include dopamine, norepinephrine, serotonin, gamma-aminobutryic acid, or glutamate. Alternatively, the compound of Formula (I) may act as an antagonist of nicotinic acetylcholine receptor function. Hence the compound of Formula (I) may decrease the extent or duration of the release of a neurotransmitter from a central nervous system tissue. In this regard, the compound of Formula (I) may act by decreasing stimulant-evoked neurotransmitter release. The neurotransmitter affected may include dopamine, norepinephrine, serotonin, gamma-aminobutryic acid, or glutamate. Alternatively, the compound of Formula (I) may act by interacting with a postsynaptic acetylcholine receptor to change the membrane potential of the cell thereby increasing or decreasing the likelihood of firing an action potential, or to alter one or more second messenger systems within the cell so as to decrease or increase the nicotinic cholinergic response.

In another embodiment, the present invention is directed to a method for preventing and/or treating a central nervous system associated disorder comprising administering to a mammalian subject in need thereof a therapeutically effective amount of a compound of Formula (I). In such a method, the compound of Formula (I) may selectively bind to one or more subtypes of nicotinic acetylcholine receptor. The compound of Formula (I) may act as an agoinst or partial agonist of nicotinic acetylcholine receptor function. Hence the compound of Formula (I) may increase or prolong the release of a neurotransmitter from a central nervous system tissue. The neurotransmitter affected may include dopamine, norepinephrine, serotonin, gamma-aminobutryic acid, or glutamate. Alternatively, the compound of Formula (I) may act as an antagonist of nicotinic acetylcholine receptor function. Hence the compound of Formula (I) may decrease the extent or duration of the release of a neurotransmitter from a central nervous system tissue. In this regard, the compound of Formula (I) may act by decreasing stimulant-evoked neurotransmitter release. The neurotransmitter affected may include dopamine, norepinephrine, serotonin, gamma-aminobutryic acid, or glutamate. Alternatively, the compound of Formula (I) may act by interacting with a postsynaptic acetylcholine receptor to change the membrane potential of the cell thereby increasing or decreasing the likelihood of firing an action potential, or to alter one or more second messenger systems within the cell so as to decrease or increase the nicotinic cholinergic response.

Central nervous system disorders which may be treated according to the method of the present invention include Alzheimer's disease, dementia, cognitive dysfunctions (including disorders of attention, focus and concentration), attention deficit disorders, affective disorders, extrapyramidal motor function disorders, Parkinson's disease, progressive supramolecular palsy, Huntington's disease, Gilles de la Tourette syndrome, tardive dyskinesia, neuroendocrine disorders, dysregulation of food intake, disorders of nociception, pain, mood and emotional disorders, depression, panic anxiety, psychosis, schizophrenia, or epilepsy.

In yet another embodiment, the present invention is directed to a method for preventing and/or treating substance use and/or abuse comprising administering to a mammalian subject in need thereof a therapeutically effective amount of a compound of Formula (I). In such a method, the compound of Formula (I) may selectively bind to one or more subtypes of nicotinic acetylcholine receptor. The compound of Formula (I) may act as an agoinst or partial agonist of nicotinic acetylcholine receptor function. Hence the compound of Formula (I) may increase or prolong the release of a neurotransmitter from a central nervous system tissue. The neurotransmitter affected may include dopamine, norepinephrine, serotonin, gamma-aminobutryic acid, or glutamate. Alternatively, the compound of Formula (I) may act as an antagonist of nicotinic acetylcholine receptor function. Hence the compound of Formula (I) may decrease the extent or duration of the release of a neurotransmitter from a central nervous system tissue. In this regard, the compound of Formula (I) may act by decreasing stimulant-evoked neurotransmitter release. The neurotransmitter affected may include dopamine, norepinephrine, serotonin, gamma-aminobutryic acid, or glutamate. Alternatively, the compound of Formula (I) may act by interacting with a postsynaptic acetylcholine receptor to change the membrane potential of the cell thereby increasing or decreasing the likelihood of firing an action potential, or to alter one or more second messenger systems within the cell so as to decrease or increase the nicotinic cholinergic response.

The conditions of substance use and/or abuse treated according to the method of the present invention include nicotine abuse (including use in smoking cessation therapy), nicotine intoxication, amphetamine abuse, methamphetamine abuse, MDMA (methylenedioxymethamphetamine) abuse, methylphenidate abuse, cocaine abuse, or alcohol abuse.

In another embodiment, the present invention is directed to a method for preventing and/or treating gastrointestinal tract disorders comprising administering to a mammalian subject in need thereof a therapeutically effective amount of a compound of Formula (I). In such a method, the compound of Formula (I) may selectively bind to one or more subtypes of nicotinic acetylcholine receptor. The compound of Formula (I) may act as an agonist or partial agonist of nicotinic acetylcholine receptor function. Hence the compound of Formula (I) may increase or prolong the release of a neurotransmitter from a central nervous system tissue, or may increase or prolong the release of a neurotransmitter from a peripheral nervous system tissue, or may act directly on a gastrointestinal tract tissue. The neurotransmitter affected may include dopamine, norepinephrine, serotonin, gamma-aminobutryic acid, or glutamate. Alternatively, the compound of Formula (I) may act as an antagonist of nicotinic acetylcholine receptor function. Hence the compound of Formula (I) may decrease the extent or duration of the release of a neurotransmitter from a central nervous system tissue, or may decrease the extent or duration of the release of a neurotransmitter from a peripheral nervous system tissue, or may act directly on a gastrointestinal tract tissue. In this regard, the compound of Formula (I) may act by decreasing stimulant-evoked neurotransmitter release. The neurotransmitter affected may include dopamine, norepinephrine, serotonin, gamma-aminobutryic acid, or glutamate. Alternatively, the compound of Formula (I) may act by interacting with a postsynaptic acetylcholine receptor to change the membrane potential of the cell thereby increasing or decreasing the likelihood of firing an action potential, or to alter one or more second messenger systems within the cell so as to decrease or increase the nicotinic cholinergic response.

Gastrointestinal disorders which may be treated according to the method of the present invention include irritable bowel syndrome, colitis, diarrhea, constipation, gastric acid secretion or ulcers.

The compounds of the present invention can be delivered directly or in pharmaceutical compositions along with suitable carriers or excipients, as is well known in the art. For example, a pharmaceutical composition of the invention may include a conventional additive, such as a stabilizer, buffer, salt, preservative, filler, flavor enhancer and the like, as known to those skilled in the art. Exemplary buffers include phosphates, carbonates, citrates and the like. Exemplary preservatives include EDTA, EGTA, BHA, BHT and the like.

An effective amount of such agents can readily be determined by routine experimentation, as can the most effective and convenient route of administration and the most appropriate formulation. Various formulations and drug delivery systems are available in the art. See, e.g., Gennaro, A. R., ed. (1995) Remington's Pharmaceutical Sciences.

Suitable routes of administration may, for example, include oral, rectal, transmucosal, nasal, or intestinal administration and parenteral delivery, including intramuscular, subcutaneous, intramedullary injections, as well as intrathecal, direct intraventricular, intravenous, intraperitoneal, intranasal, or intraocular injections. In addition, the agent or composition thereof may be administered sublingually or via a spray. The agent or composition thereof may be administered in a local rather than a systemic manner. For example, a suitable agent can be delivered via injection or in a targeted drug delivery system, such as a depot or sustained release formulation.

The pharmaceutical compositions of the present invention may be manufactured by any of the methods well-known in the art, such as by conventional mixing, dissolving, granulating, dragee-making, levigating, emulsifying, encapsulating, entrapping, or lyophilizing processes. As noted above, the compositions of the present invention can include one or more physiologically acceptable carriers such as excipients and auxiliaries that facilitate processing of active molecules into preparations for pharmaceutical use.

Proper formulation is dependent upon the route of administration chosen. For injection, for example, the composition may be formulated in aqueous solutions, preferably in physiologically compatible buffers such as Hanks' solution, Ringer's solution, or physiological saline buffer. For transmucosal or nasal administration, penetrants appropriate to the barrier to be permeated are used in the formulation. Such penetrants are generally known in the art. In a preferred embodiment of the present invention, the present compounds are prepared in a formulation intended for oral administration. For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject. The compounds may also be formulated in rectal compositions such as suppositories or retention enemas, e.g., containing conventional suppository bases such as cocoa butter or other glycerides.

Pharmaceutical preparations for oral use can be obtained as solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Also, wetting agents such as sodium dodecyl sulfate may be included.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations for oral administration include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

In one embodiment, the compounds of the present invention can be administered transdermally, such as through a skin patch, or topically. In one aspect, the transdermal or topical formulations of the present invention can additionally comprise one or multiple penetration enhancers or other effectors, including agents that enhance migration of the delivered compound. Transdermal or topical administration could be preferred, for example, in situations in which location specific delivery is desired.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide, or any other suitable gas. In the case of a pressurized aerosol, the appropriate dosage unit may be determined by providing a valve to deliver a metered amount. Capsules and cartridges of, for example, gelatin, for use in an inhaler or insufflator may be formulated. These typically contain a powder mix of the compound and a suitable powder base such as lactose or starch.

Compositions formulated for parenteral administration by injection, e.g., by bolus injection or continuous infusion can be presented in unit dosage form, e.g., in ampoules or in multi-dose containers, with an added preservative. The compositions may take such forms as suspensions, solutions, or emulsions in oily or aqueous vehicles, and may contain formulatory agents such as suspending, stabilizing and/or dispersing agents. Formulations for parenteral administration include aqueous solutions or other compositions in water-soluble form.

Suspensions of the active compounds may also be prepared as appropriate oily injection suspensions. Suitable lipophilic solvents or vehicles include fatty oils such as sesame oil and synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions. Alternatively, the active ingredient may be in powder form for constitution with a suitable vehicle, e.g., sterile pyrogen-free water, before use.

As mentioned above, the compositions of the present invention may also be formulated as a depot preparation. Such long acting formulations may be administered by implantation (for example, subcutaneously or intramuscularly) or by intramuscular injection. Thus, for example, the present compounds may be formulated with suitable polymeric or hydrophobic materials (for example as an emulsion in an acceptable oil) or ion exchange resins, or as sparingly soluble derivatives, for example, as a sparingly soluble salt.

Suitable carriers for the hydrophobic molecules of the invention are well known in the art and include co-solvent systems comprising, for example, benzyl alcohol, a nonpolar surfactant, a water-miscible organic polymer, and an aqueous phase. The co-solvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system is effective in dissolving hydrophobic compounds and produces low toxicity upon systemic administration. Naturally, the proportions of a co-solvent system may be varied considerably without destroying its solubility and toxicity characteristics. Furthermore, the identity of the co-solvent components may be varied. For example, other low-toxicity nonpolar surfactants may be used instead of polysorbate 80, the fraction size of polyethylene glycol may be varied, other biocompatible polymers may replace polyethylene glycol, e.g., polyvinyl pyrrolidone, and other sugars or polysaccharides may substitute for dextrose.

Alternatively, other delivery systems for hydrophobic molecules may be employed. Liposomes and emulsions are well known examples of delivery vehicles or carriers for hydrophobic drugs. Liposomal delivery systems are discussed above in the context of gene-delivery systems. Certain organic solvents such as dimethylsulfoxide also may be employed, although usually at the cost of greater toxicity. Additionally, the compounds may be delivered using sustained-release systems, such as semi-permeable matrices of solid hydrophobic polymers containing the effective amount of the composition to be administered. Various sustained-release materials are established and available to those of skill in the art. Sustained-release capsules may, depending on their chemical nature, release the compounds for a few weeks up to over 100 days. Depending on the chemical nature and the biological stability of the therapeutic reagent, additional strategies for stabilization may be employed.

For any composition used in the present methods of treatment, a therapeutically effective dose can be estimated initially using a variety of techniques well known in the art. For example, in a cell culture assay, a dose can be formulated in animal models to achieve a circulating concentration range that includes the $IC_{50}$ as determined in cell culture. Dosage ranges appropriate for human subjects can be determined, for example, using data obtained from cell culture assays and other animal studies.

A therapeutically effective dose of an agent refers to that amount of the agent that results in amelioration of symptoms or a prolongation of survival in a subject. Toxicity and therapeutic efficacy of such molecules can be determined by standard pharmaceutical procedures in cell cultures or experimental animals, e.g., by determining the $LD_{50}$ (the dose lethal to 50% of the population) and the $ED_{50}$ (the dose therapeutically effective in 50% of the population). The dose ratio of toxic to therapeutic effects is the therapeutic index, which can be expressed as the ratio $LD_{50}/ED_{50}$. Agents that exhibit high therapeutic indices are preferred.

Dosages preferably fall within a range of circulating concentrations that includes the $ED_{50}$ with little or no toxicity. Dosages may vary within this range depending upon the dosage form employed and the route of administration utilized. The exact formulation, route of administration, and dosage should be chosen, according to methods known in the art, in view of the specifics of a subject's condition.

The amount of agent or composition administered will, of course, be dependent on a variety of factors, including the sex, age, and weight of the subject being treated, the severity of the affliction, the manner of administration, and the judgment of the prescribing physician. The present compositions may, if desired, be presented in a pack or dispenser device containing one or more unit dosage forms containing the active ingredient. Such a pack or device may, for example, comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labeled for treatment of an indicated condition.

These and other embodiments of the present invention will readily occur to those of ordinary skill in the art in view of the disclosure herein, and are specifically contemplated.

EXAMPLES

The invention is further understood by reference to the following examples, which are intended to be purely exemplary of the invention. The present invention is not limited in scope by the exemplified embodiments, which are intended as illustrations of single aspects of the invention only. Any methods that are functionally equivalent are within the scope of the invention. Various modifications of the invention in addition to those described herein will become apparent to those skilled in the art from the foregoing description. Such modifications fall within the scope of the appended claims.

Example 1

Preparation of
1,3,5-tris-(5-hydroxypent-1-ynyl)-benzene

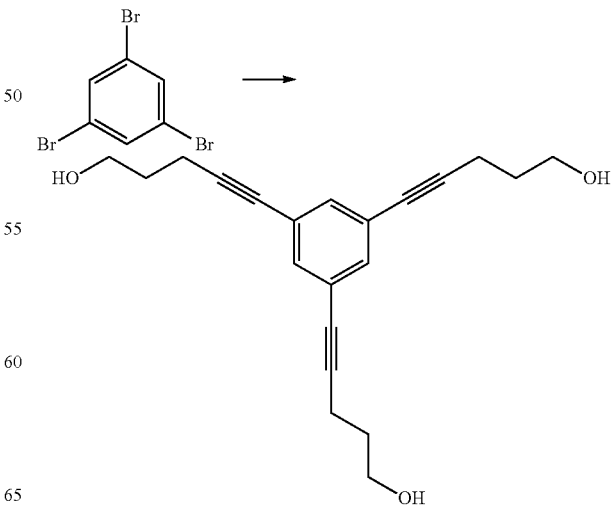

1,3,5-Tribromobenzene (10 g, 31.76 mmol), 4-pentyn-1-ol (10.69 g, 127.06 mmol) and bis(triphenylphosphine)palladium(II) dichloride were stirred in triethylamine under nitrogen for 5 minutes. Copper(I) iodide (92 mg, 0.48 mmol) was added and the mixture was stirred for 6 hours at 80° C. The mixture was cooled to room temperature, filtered through a celite pad and rinsed with ethyl acetate. The combined filtrate was evaporated to dryness under reduced pressure. The resulting residue was purified by column chromatography (CHCl$_3$:MeOH 10:1) to afford 7.61 g of 1,3,5-tris-(5-hydroxy-1-pentynyl)-benzene. Yield: 74%. $^1$H NMR (300 MHz, CDCl$_3$) δ 7.31 (3, 3h), 3.81 (t, J=6.0 Hz, 6H), 2.52 (t, J=6.9 Hz, 6H), 1.85 (m, 6H); $^{13}$C NMR (75 MHz, CDCl$_3$) δ 133.8, 124.2, 90.5, 80.0, 61.9, 31.5, 16.2 ppm.

Example 2

Preparation of 1,3,5-tris-(5-bromopent-1-ynyl)-benzene

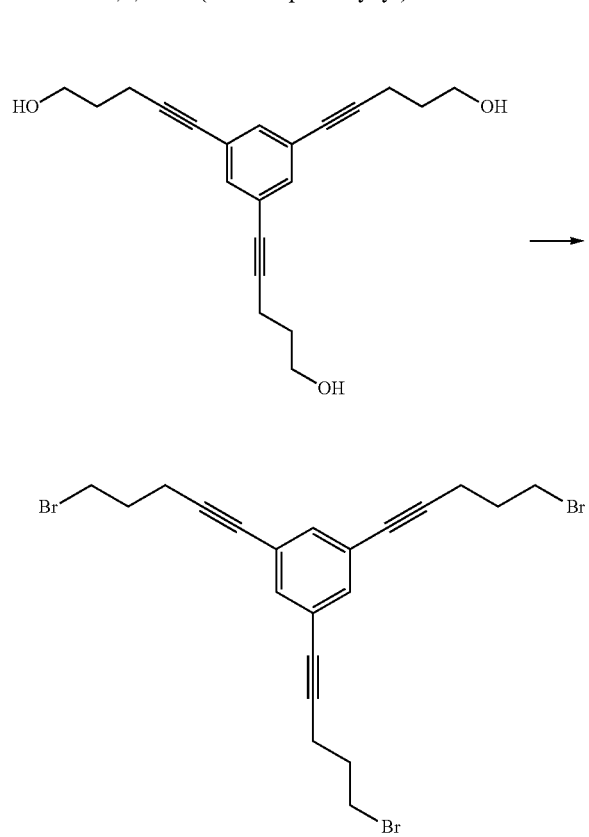

1,3,5-tris-(5-hydroxy-1-pentynyl)-benzene (1.86 g, 5.73 mmol) and carbon tetrabromide (7.41 g, 22.35 mmol) were dissolved in dry methylene chloride (40 mL) and cooled to 0° C. Triphenyl phosphine (6.16 g, 23.47 mmol) was added dropwide and the mixture was stirred at 0° C. for 30 minutes. The mixture was poured into hexanes (200 mL), filtered through a short silica gel column and washed with ethyl acetate/hexanes (1/4). The combined organic solvents were evaporated to dryness under reduced pressure. The resulting residue was purified by column chromatography (hexanes:ethyl acetate 10:1) to afford 2.63 g of 1,3,5-tris-(5-bromopent-1-ynyl)-benzene. Yield 89%. $^1$H NMR (300 MHz, CDCl$_3$) δ 7.33 (s, 3H), 3.57 (t, J=6.3 Hz), 2.60 (t, J=6.9 Hz, 6H), 2.12 (m, 6H) ppm; $^{13}$C NMR (75 MHz, CDCl$_3$) δ 133.9, 124.1, 89.2, 80.4, 32.6, 31.7, 18.4 ppm.

Example 3

Preparation of 1,3,5-tris-(5-hydroxypentyl)-benzene

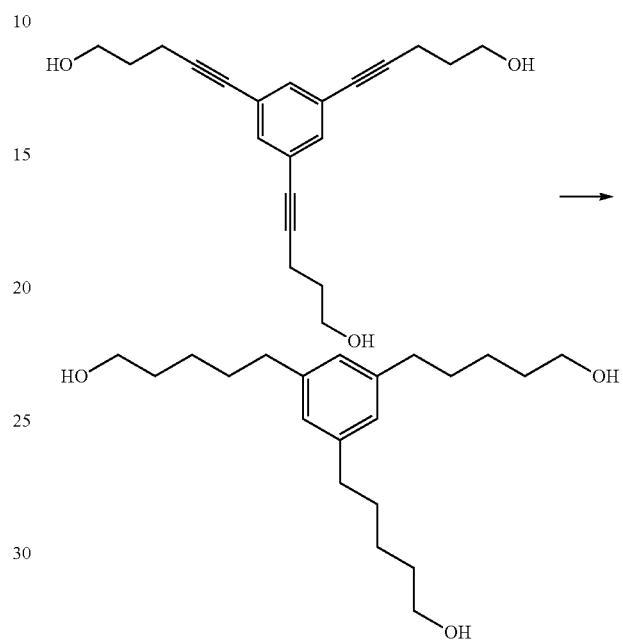

1,3,5-tris-(5-hydroxy-1-pentynyl)-benzene (2.84 g, 8.6 mmol) was dissolved in methanol (30 mL) and 10% Pd/C (5% w/w) was added. The resulting mixture was hydrogenated on a Parr hydrogenation apparatus (45 psi) for 4 hours. The catalyst was removed by filtration through a celite pad. The filter cake was rinsed with methanol, and the combined organic liquors were concentrated under reduced pressure. The crude product was purified by column chromatography (CHCl$_3$:MeOH 6:1) to afford 2.84 g of 1,3,5-tris-(5-hydroxypentyl)-benzene. Yield 96%. $^1$H NMR (300 MHz, CDCl$_3$) δ 6.81 (s, 3H), 3.62 (t, J=6.3 Hz, 6H), 2.57 (t, J=7.5 Hz, 6H), 1.53-1.70 (m, 12H), 1.38 (m, 6H) ppm; $^{13}$C NMR (75 MHz, CDCl$_3$) δ 142.5, 126.1, 63.1, 36.1, 32.9, 31.5, 25.7 ppm.

Example 4

Preparation of 1,3,5-tris-(5-bromopentyl)-benzene

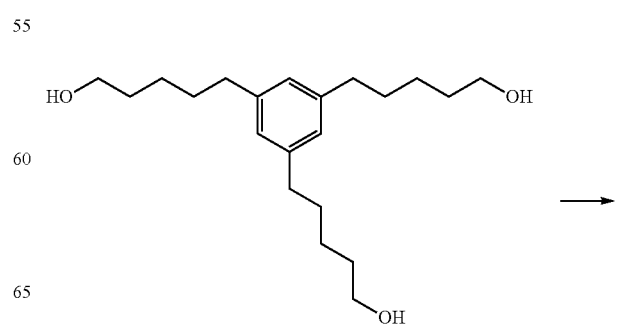

-continued

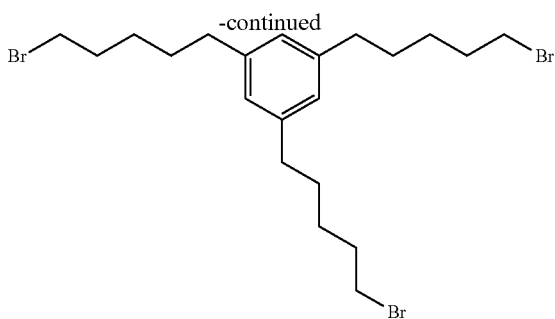

Preparation of 1,3,5-tris-(5-bromopentyl)-benzene 1,3,5-tris-(5-hydroxypentyl)-benzene (2.83 g, 8.41 mmol) and carbon tetrabromide (10.99 g, 32.80 mmol) were dissolved in dry methylene chloride (50 mL) and cooled to 0° C. Triphenyl phosphine (9.03 g, 34.33 mmol) was added dropwise and the mixture was stirred for 30 minutes at 0° C. The mixture was poured into hexanes (250 mL), filtered through a short silica gel column and washed with ethyl acetate/hexanes (1/4). The combined organic solvents were evaporated to dryness under reduced pressure. The resulting residue was purified by column chromatography (hexanes:ethyl acetate 8:1) to afford 4.08 g of 1,3,5-tris-(5-bromopentyl)-benzene. Yield 92%. $^1$H NMR (300 MHz, CDCl$_3$) δ 6.81 (s, 3h), 3.41 (t, J=6.9 Hz, 6H), 2.60 (t, J=7.5 Hz, 6H), 1.88 (m, 6H), 1.45 (m, 6H) ppm; $^{13}$C NMR (75 MHz, CDCl$_3$) δ 142.4, 126.1, 35.9, 34.2, 32.9, 30.9, 28.2 ppm.

Example 5

Preparation of 1,3,5-tris-[5-(2-picolinium)-pent-1-ynyl]-benzene tribromide

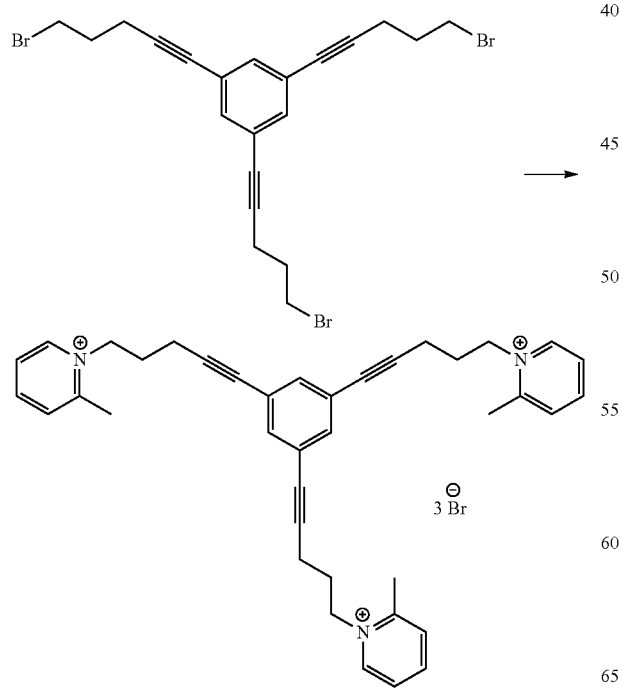

A mixture of 1,3,5-tris-(5-bromopent-1-ynyl)-benzene (223 mg, 0.43 mmol) and 2-picoline (607 mg, 6.52 mmol) was heated at 60-70° C. for 12 hours. The resultant mixture was washed with diethyl ether and then dissolved in water (15 mL), the aqueous solution was washed with diethyl ether, then lyophilized to afford 327 mg of 1,3,5-tris-[5-(2-picolinium)-pent-1-ynyl]-benzene tribromide. Yield 95%. $^1$H NMR (300 MHz, CD$_3$OD) δ 9.01 (dd, J=6.3, 0.9 Hz, 3H), 8.44 (dt, J=7.8, 1.5 Hz, 3H), 7.92-8.07 (m, 6H), 7.41 (s, 3H), 4.81 (t, J=6.0 Hz), 2.98 (s, 9H), 2.70 (t, J=7.2 Hz, 6H), 2.29 (m, 6H) ppm; $^{13}$C NMR (75 MHz, CD$_3$OD) δ 157.1, 146.8, 146.6, 134.9, 131.6, 127.1, 125.4, 90.1, 81.6, 58.4, 29.9, 20.7, 17.3 ppm.

Example 6

Preparation of 1,3,5-tris-[5-(3-picolinium)-pent-1-ynyl]-benzene tribromide

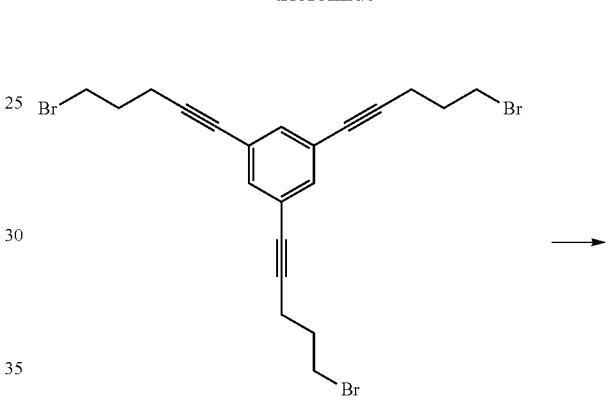

A mixture of 1,3,5-tris-(5-bromopent-1-ynyl)-benzene (256 mg, 0.50 mmol) and 3-picoline (690 mg, 7.50 mmol) was heated at 60-70° C. for 12 hours. The resultant mixture was washed with diethyl ether (30 mL×3) and then dissolved in water (15 mL), the aqueous solution was washed with diethyl ether, then lyophilized to afford 345 mg of 1,3,5-tris-[5-(3-picolinium)-pent-1-ynyl]-benzene tribromide. Yield 87%. $^1$H NMR (300 MHz, CD$_3$OD) δ 9.02 (s, 3H), 8.92 (d, J=6.0 Hz, 3H), 8.4 (d, J=8.4 Hz, 3H), 8.01 (dd, J=8.1, 6.0 Hz, 3H), 7.35 (s, 3H), 4.81 (t, J=7.2 Hz, 6H), 2.64 (t, J=6.9 Hz, 6H), 2.58 (s, 9H), 2.35 (m, 6H) ppm; $^{13}$C NMR (75 MHz, CD$_3$OD) δ 147.5, 145.8, 143.4, 141.3, 134.9, 128.8, 125.3, 89.9, 81.5, 62.2, 31.0, 18.7, 17.2 ppm.

Example 7

Preparation of 1,3,5-tris-[5-(4-picolinium)-pent-1-ynyl]-benzene tribromide

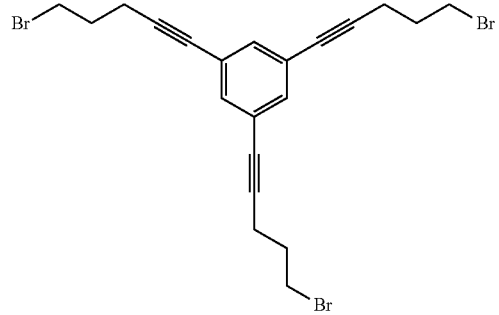

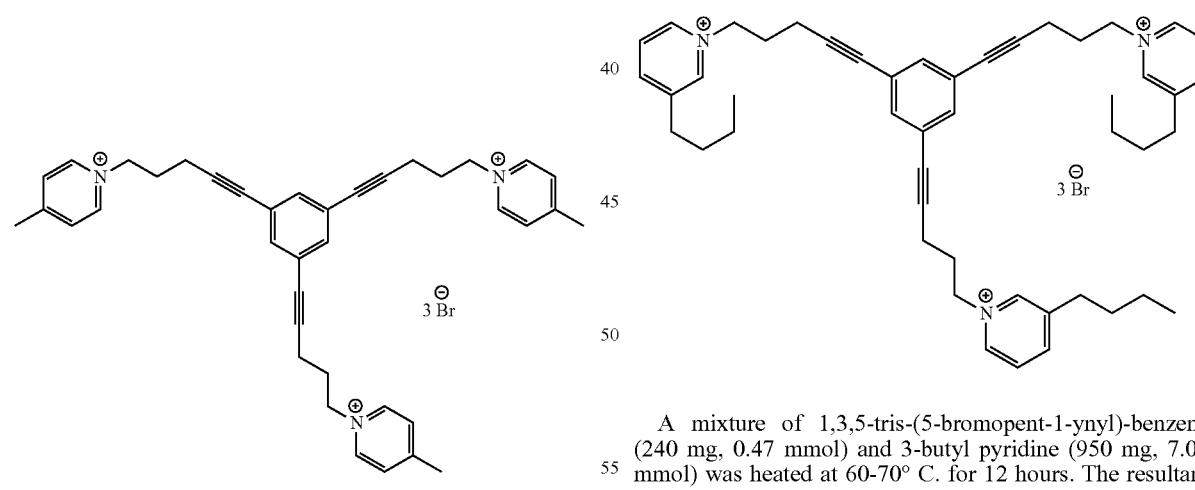

A mixture of 1,3,5-tris-(5-bromopent-1-ynyl)-benzene (210 mg, 0.41 mmol) and 4-picoline (572 mg, 6.14 mmol) was heated at 60-70° C. for 12 hours. The resultant mixture was washed with diethyl ether and then dissolved in water (15 mL), the aqueous solution was washed with diethyl ether (30 mL×3), then lyophilized to afford 316 mg of 1,3,5-tris-[5-(4-picolinium)-pent-1-ynyl]-benzene tribromide. Yield 97%. $^1$H NMR (300 MHz, CD$_3$OD) 8.91 (dd, J=5.1, 1.8 Hz, 6H), 7.94 (d, J=6.3 Hz, 6H), 4.77 (t, J=6.9 Hz, 6H), 2.63 (t, J=6.6 Hz, 6H), 2.62 (s, 9H), 2.33 (m, 6H) ppm; $^{13}$C NMR (75 MHz, CD$_3$OD) δ 161.5, 145.2, 134.9, 130.0, 125.4, 90.0, 81.4, 61.6, 30.8, 22.2, 17.2 ppm.

Example 8

Preparation of 1,3,5-tris-[5-(3-butyl-pyridinium)-pent-1-ynyl]-benzene tribromide

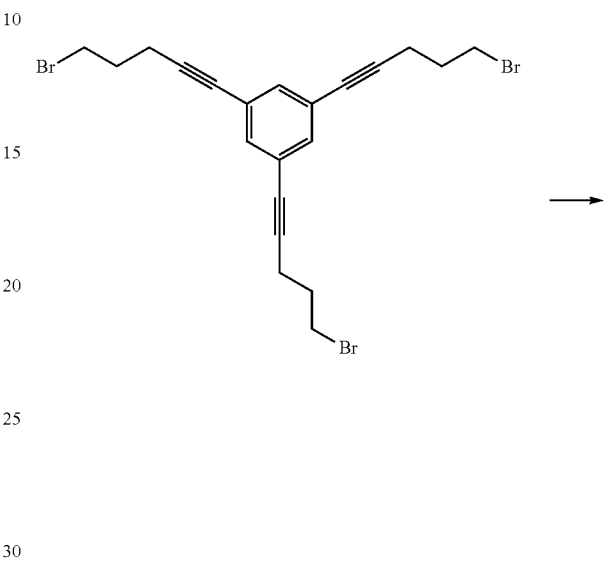

A mixture of 1,3,5-tris-(5-bromopent-1-ynyl)-benzene (240 mg, 0.47 mmol) and 3-butyl pyridine (950 mg, 7.05 mmol) was heated at 60-70° C. for 12 hours. The resultant mixture was washed with diethyl ether and then dissolved in water (15 mL), the aqueous solution was washed with diethyl ether (30 mL×3), then lyophilized to afford 254 mg of 1,3,5-tris-[5-(3-butyl-pyridinium)-pent-1-ynyl]-benzene tribromide. Yield 59%. $^1$H NMR (300 MHz, CD$_3$OD) δ 9.04 (s, 3H), 8.94 (d, J=6.0 Hz, 3H), 8.44 (d, J=8.1 Hz, 3H), 8.04 (dd, J=8.1, 6.0 Hz, 3H), 7.33 (s, 3H), 4.82 (t, J=7.2 Hz, 6H), 2.87 (t, J=7.8 Hz, 6H), 2.63 (t, J=6.9 Hz, 6H), 2.35 (m, 6H), 1.69 (m, 6H), 1.42 (m, 6H), 0.97 (t, J=7.5 Hz, 9H) ppm; $^{13}$C NMR (75 MHz, CD$_3$OD) δ 146.8, 145.8, 145.6, 143.6, 135.0, 129.0, 125.3, 89.9, 81.5, 62.2, 33.8, 33.5, 30.9, 23.5, 17.2, 14.3 ppm.

Example 9

Preparation of 1,3,5-tris-[5-(3-phenyl-pyridinium)-pent-1-ynyl]-benzene tribromide

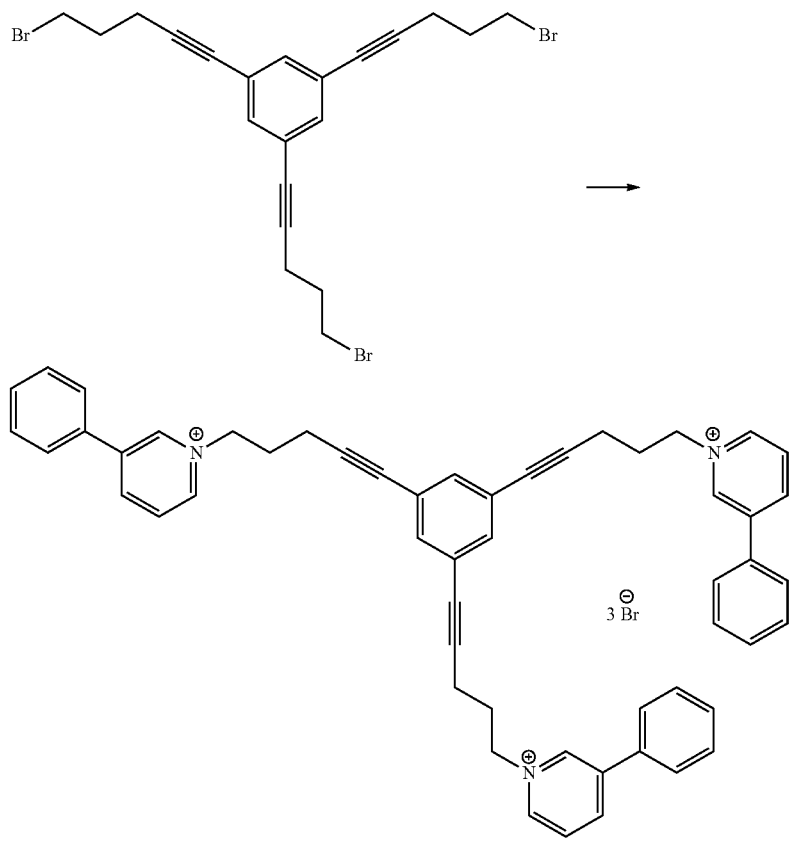

A mixture of 1,3,5-tris-(5-bromopent-1-ynyl)-benzene (259 mg, 0.50 mmol) and 3-phenyl pyridine (1.18 g, 7.50 mmol) was heated at 60-70° C. for 12 hours. The resultant mixture was washed with diethyl ether and then dissolved in water (15 mL), the aqueous solution was washed with diethyl ether (30 mL×5), then lyophilized to afford 415 mg of 1,3,5-tris-[5-(3-phenyl-pyridinium)-pent-1-ynyl]-benzene tribromide. Yield 85%. $^1$H NMR (300 MHz, CD$_3$OD) δ 9.50 (s, 3H), 9.09 (d, J=6.0 Hz, 3H), 8.78 (d, J=8.1 Hz, 3H), 8.16 (dd, J=8.1, 6.0 Hz, 3H), 7.75-7.87 (m, 6H), 7.42-7.65 (m, 9H), 7.17 (s, 3H), 4.96 (t, J=6.9 Hz, 6H), 2.69 (t, J=6.3 Hz, 6H), 2.42 (m, 6H) ppm; $^{13}$C NMR (75 MHz, CD$_3$OD) δ 144.4, 144.3, 144.2, 142.6, 134.9, 134.5, 131.5, 130.8, 129.5, 128.7, 125.1, 90.0, 81.5, 62.6, 30.8, 17.4 ppm.

Example 10

Preparation of 1,3,5-tris-{5-[3-(1-methyl-2-S-pyrrolidinyl)pyridinium]-pent-1-ynyl}-benzene tribromide

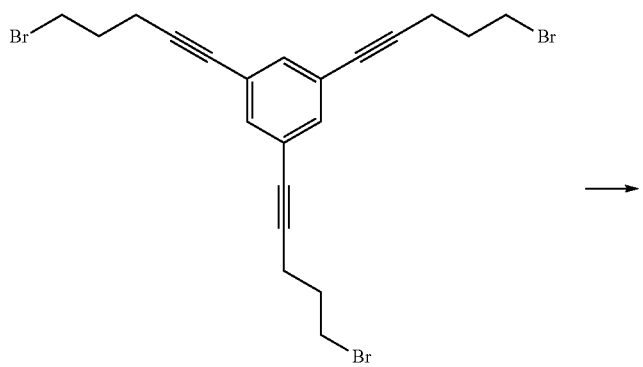

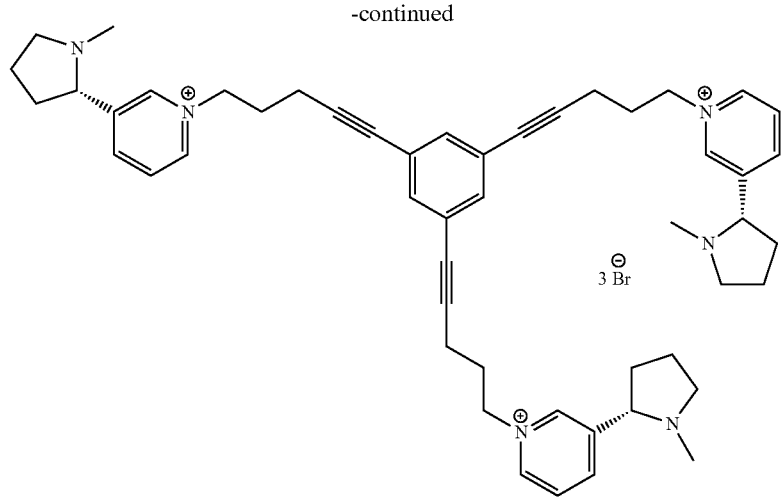

A mixture of 1,3,5-tris-(5-bromopent-1-ynyl)-benzene (246 mg, 0.48 mmol) and S-nicotine (1.5 mL) was heated at 60-70° C. for 12 hours. The resultant mixture was washed with diethyl ether and then dissolved in water (15 mL), the aqueous solution was washed with diethyl ether (30 mL×5), then lyophilized to afford 440 mg of 1,3,5-tris-{5-[3-(1-methyl-2-S-pyrrolidinyl)pyridinium]-pent-1-ynyl}-benzene tribromide. Yield 92%. $^1$H NMR (300 MHz, CD$_3$OD) δ 9.16 (s, 3H), 9.02 (d, J=6.0 Hz, 3H), 8.60 (d, j=8.1 Hz, 3H), 8.12 (dd, J=8,1, 6.0 Hz, 3H), 7.40 (s, 3H), 4.86 (t, J=6.9 Hz, 6H), 3.69 (m, 3H), 3.32 (m, 6H), 2.14-2.70 (m, 12H), 2.33 (s, 9H), 1.73-2.14 (m, 10H) ppm; $^{13}$C NMR (75 MHz, CD$_3$OD) δ 146.2, 145.4, 145.0, 135.1, 129.5, 125.3, 89.8, 81.8, 68.8, 62.3, 58.0, 40.8, 36.0, 30.8, 24.1, 17.1 ppm.

Example 11

Preparation of 1,3,5-tris-[5-(1-quinolinium)-pent-1-ynyl]-benzene tribromide

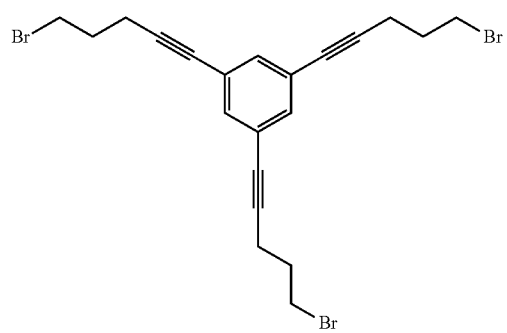

→

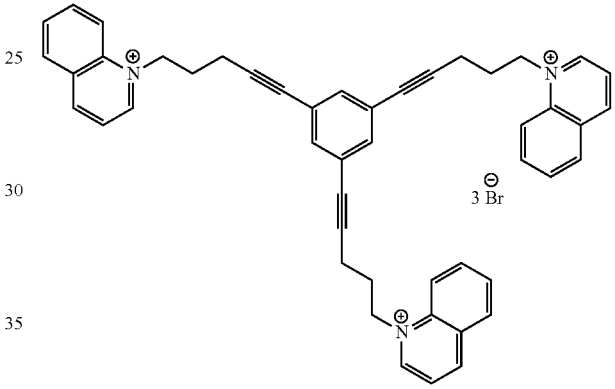

A mixture of 1,3,5-tris-(5-bromopent-1-ynyl)-benzene (232 mg, 0.45 mmol) and quinoline (880 mg, 6.75 mmol) was heated at 60-70° C. for 12 hours. The resultant mixture was washed with diethyl ether and then dissolved in water (15 mL), the aqueous solution was washed with diethyl ether (30 mL×5), then lyophilized to afford 234 mg of 1,3,5-tris-[5-(1-quinolinium)-pent-1-ynyl]-benzene tribromide. Yield 58%. $^1$H NMR (300 MHz, CD$_3$OD) δ 9.58 (dd, J=6.0, 4.5 Hz, 3H), 9.18 (d, J=8.1 Hz, 3H), 8.67, d, J=9.0 Hz, 3H), 8.41 (dd, J=8.1, 1.8 Hz, 3H), 8.31 (m, 3H), 7.98-8.18 (m, 6H), 7.11 (s, 3H), 132 (t, J=6.9 Hz, 6H), 2.75 (t, J=6.6 Hz, 6H), 2.46 (m, 6H) ppm; $^{13}$C NMR (75 MHz, CD$_3$OD) δ 150.9, 149.3, 139.6, 137.4, 134.8, 132.3, 131.8, 131.4, 125.2, 123.2, 119.8, 90.2, 81.4, 58.8, 29.6, 17.5 ppm.

Example 12
Preparation of 1,3,5-tris-[5-(2-isoquinolinium)-pent-1-ynyl]-benzene tribromide
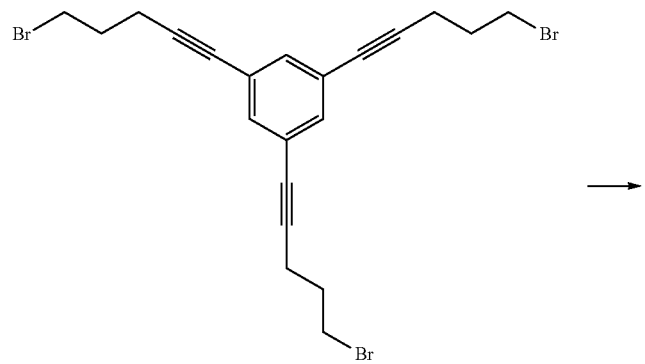
→
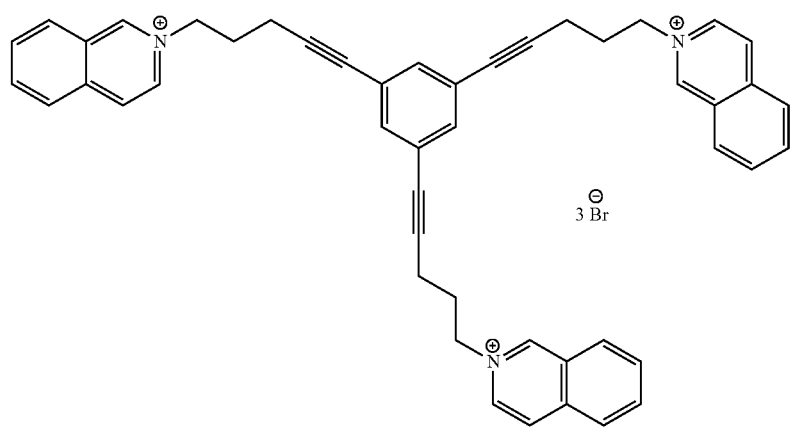

A mixture of 1,3,5-tris-(5-bromopent-1-ynyl)-benzene (222 mg, 0.43 mmol) and isoquinoline (840 mg, 6.45 mmol) was heated at 60-70° C. for 12 hours. The resultant mixture was washed with diethyl ether and then dissolved in water (15 mL), the aqueous solution was washed with diethyl ether (30 mL×5), then lyophilized to afford 357 mg of 1,3,5-tris-[5-(2-isoquinolinium)-pent-1-ynyl]-benzene tribromide. Yield 92%. $^1$H NMR (300 MHz, CD$_3$OD) δ 10.15 (s, 3H), 8.79 (dd, J=6.9, 1.2 Hz, 3H), 8.67, d, J=9.0 Hz, 3H), 8.50 (m, 3H), 8.20 (m, 6H), 8.06 (m, 3H), 6.54 (s, 3H), 5.00 (t, J=6.9 Hz, 6H), 2.75 (t, J=6.3 Hz, 6H), 2.47 (m, 6H) ppm; $^{13}$C NMR (75 MHz, CD$_3$OD) δ 151.5, 139.2, 138.5, 136.0, 134.1, 132.6, 131.6, 129.2, 128.4, 127.5, 124.7, 90.0, 81.2, 62.6, 30.5, 17.6 ppm.

Example 13

Preparation of 1,3,5-tris-[5-(3,5-lutidinium)-pent-1-ynyl]-benzene tribromide

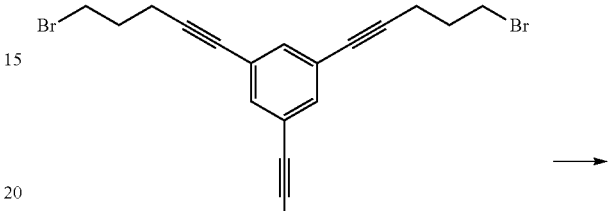

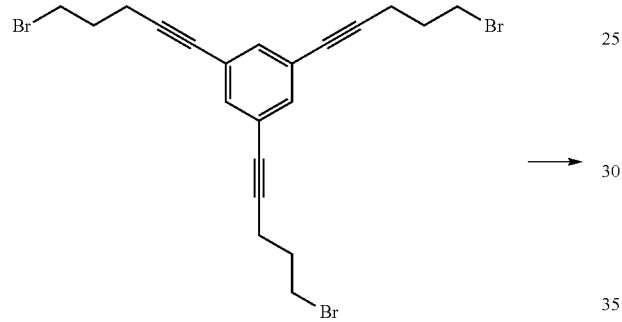

A mixture of 1,3,5-tris-(5-bromopent-1-ynyl)-benzene (252 mg, 0.49 mmol) and 3,5-lutidine (790 mg, 7.35 mmol) was heated at 60-70° C. for 12 hours. The resultant mixture was washed with diethyl ether and then dissolved in water (15 mL), the aqueous solution was washed with diethyl ether (30 mL×3), then lyophilized to afford 383 mg of 1,3,5-tris-[5-(3,5-lutidinium)-pent-1-ynyl]-benzene tribromide. Yield: 94%. $^1$H NMR (300 MHz, CD$_3$OD) δ 8.83 (s, 6H), 8.22 (s, 3H), 7.32 (s, 3H), 4.75 (t, J=7.2 Hz, 6H), 2.64 (t, J=6.6 Hz, 6H), 2.53 (s, 18H), 2.35 (m, 6H) ppm; $^{13}$C NMR (75 MHz, CD$_3$OD) δ 148.0, 143.1, 140.4, 134.9, 125.3, 90.1, 81.4, 62.0, 30.9, 18.6, 17.3 ppm.

Example 14

Preparation of 1,3,5-tris-[5-(3,4-lutidinium)-pent-1-ynyl]-benzene tribromide

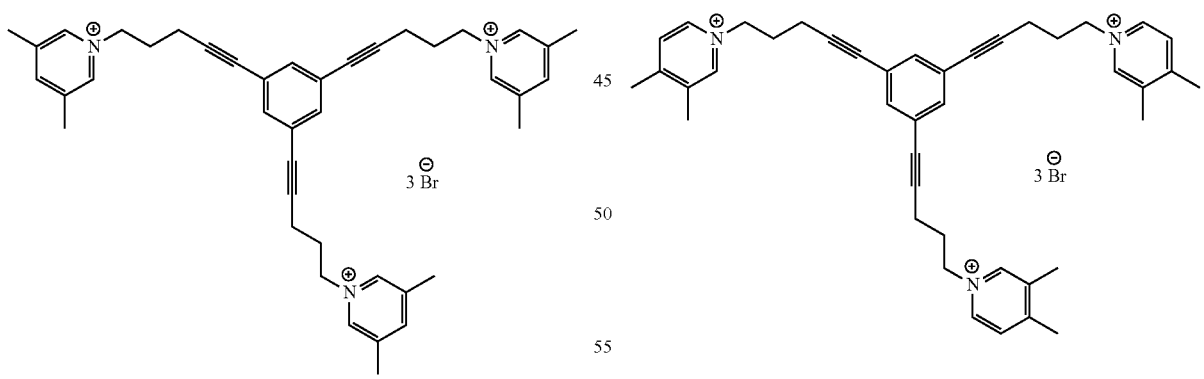

A mixture of 1,3,5-tris-(5-bromopent-1-ynyl)-benzene (235 mg, 0.46 mmol) and 3,4-lutidine (740 mg, 6.90 mmol) was heated at 60-70° C. for 12 hours. The resultant mixture was washed with diethyl ether and then dissolved in water (15 mL), the aqueous solution was washed with diethyl ether (30 mL×3), then lyophilized to afford 319 mg of 1,3,5-tris-[5-(3,4-lutidinium)-pent-1-ynyl]-benzene tribromide. Yield: 83%. $^1$H NMR (300 MHz, CD$_3$OD) δ 8.91 (s, 3H), 8.80 (dd, J=6.0, 0.9 Hz, 3H), 7.88 (d, J=6.0 Hz, 3H), 7.21 (s, 3H), 4.75 (t, J=6.9 Hz, 6H), 2.65 (t, J=6.6 Hz, 6H), 2.51 (s, 9H), 2.45 (s, 9H), 2.35 (m, 6H) ppm; $^{13}$C NMR (75 MHz, CD$_3$OD) δ

160.1, 144.5, 142.9, 139.8, 134.7, 129.6, 125.3, 90.3, 81.2, 61.5, 30.7, 20.4, 17.3, 17.2 ppm Example 15

Preparation of 1,3,5-tris-[5-(2-picolinium)-pentyl]-benzene tribromide

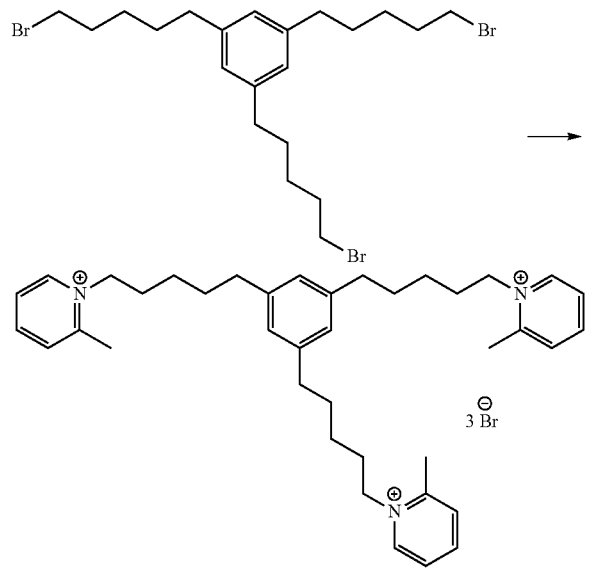

A mixture of 1,3,5-tris-(5-bromopentyl)-benzene (247 mg, 0.47 mmol) and 2-picoline (657 mg, 7.05 mmol) was heated at 60-70° C. for 12 hours. The resultant mixture was washed with diethyl ether and then dissolved in water (15 mL), the aqueous solution was washed with diethyl ether (30 mL×3), then lyophilized to afford 335 mg of 1,3,5-tris-[5-(2-picolinium)-pentyl]-benzene tribromide. Yield: 89%. $^1$H NMR (300 MHz, CD$_3$OD) δ 8.92 (dd, J=6.3, 1.5 Hz, 3H), 8.43 (dt, J=7.8, 1.5 Hz, 3H), 8.00 (d, J=7.8 Hz, 3H), 7.91 (t, J=6.3 Hz, 3H), 6.89 (s, 3H), 4.60 (t, J=7.8 Hz, 6H), 2.90 (s, 9H), 2.61 (t, J=7.5 Hz, 6H), 1.99 (m, 6H), 1.72 (m, 6H), 1.51 (m, 6H) ppm; $^{13}$C NMR (75 MHz, CD$_3$OD) δ 156.7, 146.5, 146.3, 143.4, 131.5, 127.2, 126.9, 59.3, 36.7, 32.2, 31.2, 27.1, 20.7 ppm.

Example 16

Preparation of 1,3,5-tris-[5-(3-picolinium)-pentyl]benzene tribromide

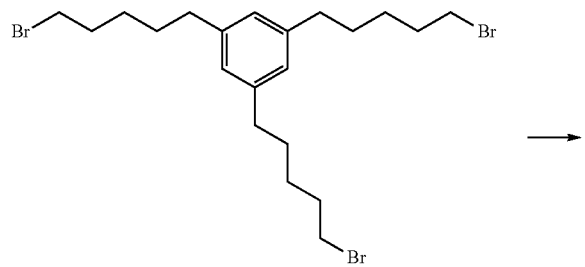

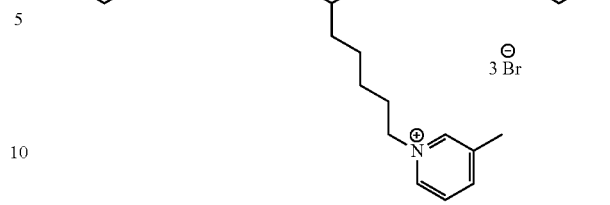

A mixture of 1,3,5-tris-(5-bromopentyl)-benzene (266 mg, 0.51 mmol) and 3-picoline (712 mg, 7.65 mmol) was heated at 60-70° C. for 12 hours. The resultant mixture was washed with diethyl ether and then dissolved in water (15 mL), the aqueous solution was washed with diethyl ether (30 mL×3), then lyophilized to afford 335 mg of 1,3,5-tris-[5-(2-picolinium)-pentyl]-benzene tribromide. Yield: 88%. $^1$H NMR (300 MHz, CD$_3$OD) δ 8.94 (s, 3H), 8.84 (d, J=6.0 Hz, 3H), 8.42 (d, J=8.4 Hz, 3H), 7.98 (dd, J=8.1, 6.0 Hz, 3H), 6.86 (s, 3H), 4.62 (t, J=7.8 Hz, 6H), 2.59 (s, 9H), 2.57 (t, J=7.5 Hz, 6H), 2.06 (m, 6H), 1.69 (m, 6H), 1.43 (m, 6H) ppm; $^{13}$C NMR (75 MHz, CD$_3$OD) δ 147.2, 145.5, 143.4, 143.0, 141.2, 128.7, 127.2, 62.9, 36.7, 32.5, 32.2, 27.0, 18.7 ppm.

Example 17

Preparation of 1,3,5-tris-[5-(4-picolinium)-pentyl]-benzene tribromide

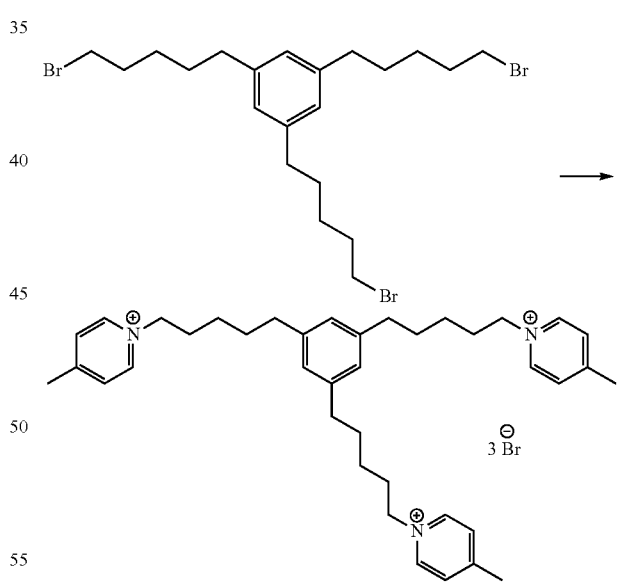

A mixture of 1,3,5-tris-(5-bromopentyl)-benzene (245 mg, 0.47 mmol) and 4-picoline (657 mg, 7.05 mmol) was heated at 60-70° C. for 12 hours. The resultant mixture was washed with diethyl ether and then dissolved in water (15 mL), the aqueous solution was washed with diethyl ether (30 mL×3), then lyophilized to afford 351 mg of 1,3,5-tris-[5-(2-picolinium)-pentyl]-benzene tribromide. Yield: 93%. $^1$H NMR (300 MHz, CD$_3$OD) δ 8.87 (d, J=6.6 Hz, 6H), 7.94 (d, J=6.6 Hz, 6H), 6.84 (s, 3H), 4.61 (t, J=7.5 Hz, 6H), 2.69 (s, 9H), 2.57 (t, J=7.5 Hz, 6H), 2.05 (m, 6H), 1.68 (m, 6H), 1.41 (m, 6H) ppm; $^{13}$C NMR (75 MHz, CD$_3$OD) δ 161.0, 144.8, 143.4, 129.9, 127.2, 62.1, 36.6, 32.4, 32.1, 26.8, 22.2 ppm.

Example 18

Preparation of 1,3,5-tris-[5-(3-butyl-pyridinium)-pentyl]-benzene tribromide

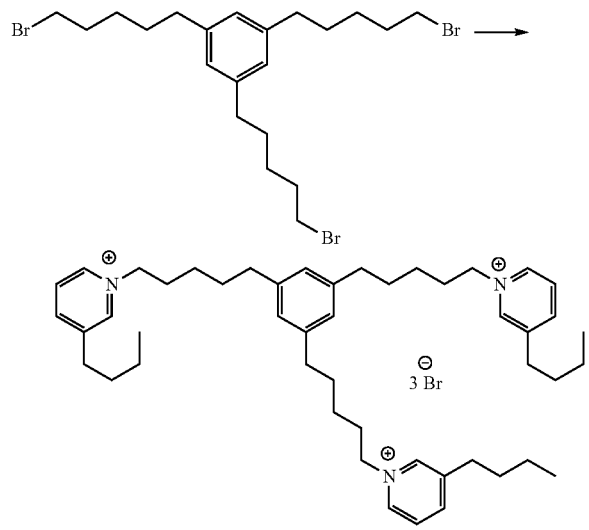

A mixture of 1,3,5-tris-(5-bromopentyl)-benzene (245 mg, 0.47 mmol) and 3-butyl-pyridine (265 mg, 1.86 mmol) was dissolved in butanone (5 mL) and heated at reflux for 24 hours. The resultant mixture was washed with diethyl ether and then dissolved in water (15 mL), the aqueous solution was washed with diethyl ether (30 mL×5), then lyophilized to afford 252 mg of 1,3,5-tris-[5-(3-butyl-pyridinium)-pentyl]-benzene tribromide. Yield: 55%. $^1$H NMR (300 MHz, CD$_3$OD) δ 9.00 (s, 3H), 8.86 (dd, J=6.3, 0.6 Hz, 3H), 8.46 (d, J=7.8 Hz, 3H), 8.01 (dd, J=7.8, 6.3 Hz, 3H), 6.84 (s, 3H), 4.64 (t, J=7.5 Hz, 6H), 2.89 (t, J=7.8 Hz, 6H), 2.58 (t, J=6.6 Hz, 6H), 2.07 (m, 6H), 1.65-1.80 (m, 12H), 1.35-1.52 (m, 12H), 0.98 (t, J=7.2 Hz, 9H) ppm; $^{13}$C NMR (75 MHz, CD$_3$OD) δ 146.6, 145.7, 145.2, 143.4, 128.9, 127.2, 62.9, 36.7, 33.9, 33.4, 32.6, 32.2, 27.0, 23.4, 14.3 ppm.

Example 19

Preparation of 1,3,5-tris-[5-(3-phenyl-pyridinium)-pentyl]-benzene tribromide

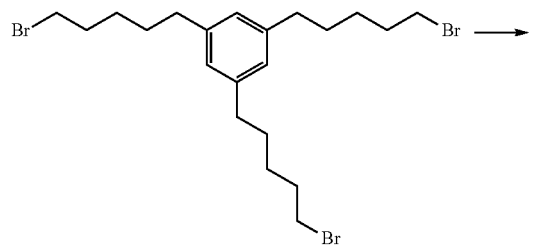

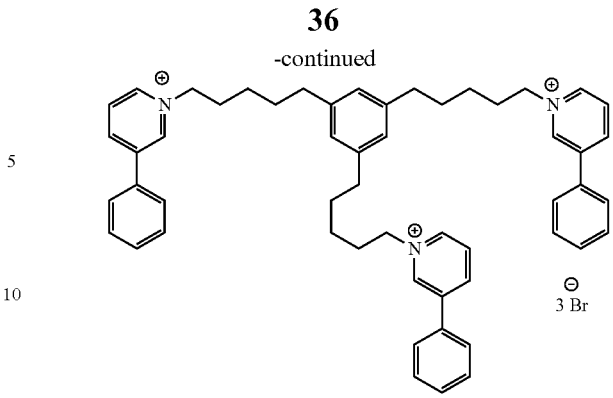

A mixture of 1,3,5-tris-(5-bromopentyl)-benzene (272 mg, 0.52 mmol) and 3-phenyl-pyridine (323 mg, 2.08 mmol) was dissolved in butanone (5 mL) and heated at reflux for 24 hours. The resultant mixture was washed with diethyl ether and then dissolved in water (15 mL), the aqueous solution was washed with diethyl ether (30 mL×5), then lyophilized to afford 215 mg of 1,3,5-tris-[5-(3-butyl-pyridinium)-pentyl]-benzene tribromide. Yield: 42%. $^1$H NMR (300 MHz, CD$_3$OD) δ 9.39 (s, 3H), 8.98 (d, J=6.0 Hz, 3H), 8.85 (ddd, J=6.0, 1.8, 1.2 Hz, 3H), 8.15 (dd, J=8.1, 6.0 Hz, 3H), 7.78-7.90 (m, 6H), 7.50-7.65 (m, 9H), 6.82 (s, 3H), 4.74 (t, 7.8 Hz, 6H), 2.55 (t, J=7.6 Hz, 6H), 2.11 (m, 6H), 1.69 (m, 6H), 1.45 (m, 6H) ppm; $^{13}$C NMR (75 MHz, CD$_3$OD) δ 144.2, 143.9, 143.4, 142.8, 134.6, 131.5, 130.8, 129.4, 128.7, 127.2, 63.3, 36.7, 32.7, 32.2, 27.0 ppm.

Example 20

Preparation of 1,3,5-tris-{5-[3-(1-methyl-2-S-pyrrodinyl)pyridinium]-pentyl}-benzene tribromide

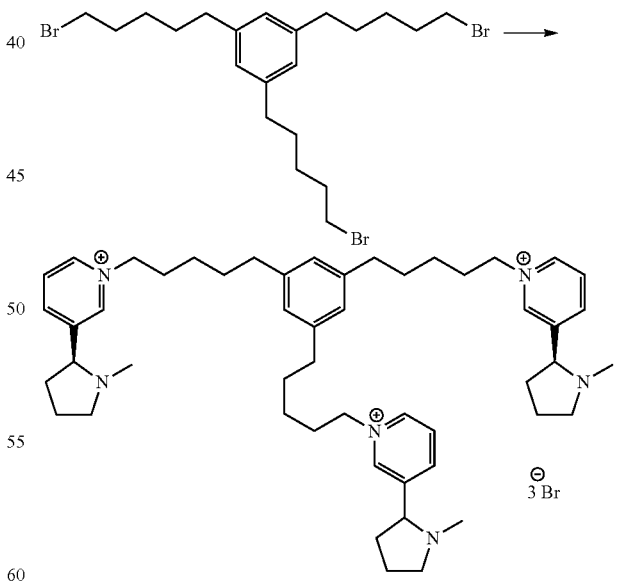

A mixture of 1,3,5-tris-(5-bromopentyl)-benzene (297 mg, 0.57 mmol) and S-nicotine (1.5 mL) was heated at 60-70° C. for 12 hours. The resultant mixture was washed with diethyl ether and then dissolved in water (15 mL), the aqueous solution was washed with diethyl ether (30 mL×5), then lyophilized to afford 510 mg of 1,3,5-tris-{5-[3-(1-methyl-2-S- pyrrolidinyl)pyridinium]-pentyl}-benzene tribromide. Yield 89%. ¹H NMR (300 MHz, CD₃OD) δ 9.08 (s, 3H), 8.94 (d, J=6.0 Hz, 3H), 8.61 (d, J=8.1 Hz, 3H), 8.08 (dd, J=8.1, 6.0 Hz, 3H), 6.83 (s, 3H), 4.67 (t, J=7.5 Hz, 6H), 3.68 (t, 7.5 Hz, 3H), 3.37 (m, 6H), 2.35-2.65 (m, 12H), 2.32 (s, 9H), 1.75-2.17 (m, 12H), 1.69 (m, 6H), 1.43 (m, 6H) ppm; ¹³C NMR (75 MHz, CD₃OD) δ 145.8, 145.1, 144.8, 143.4, 129.4, 127.2, 68.8, 63.1, 58.0, 40.7, 36.7, 36.0, 32.6, 32.2, 27.0, 24.0 ppm.

Example 21

Preparation of 1,3,5-tris-[5-(1-quinolinium)-pentyl]-benzene tribromide

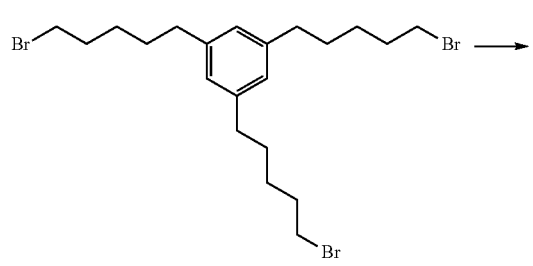

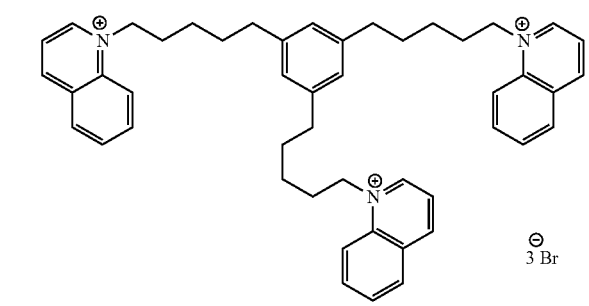

A mixture of 1,3,5-tris-(5-bromopentyl)-benzene (251 mg, 0.48 mmol) and quinoline (930 mg, 7.20 mmol) was heated at 60-70° C. for 12 hours. The resultant mixture was washed with diethyl ether and then dissolved in water (15 mL), the aqueous solution was washed with diethyl ether (30 mL×5), then lyophilized to afford 390 mg of 1,3,5-tris-[5-(1-quinolinium)-pentyl]-benzene tribromide. Yield 89%. ¹H NMR (300 MHz, CD₃OD) δ 9.46 (dd, J=6.0, 1.5 Hz, 3H), 9.22 (d, J=8.4 Hz, 3H), 8.57 (d, J=9.0 Hz, 3H), 8.45 (dd, J=8.4, 1.5 Hz, 3H), 8.30 (m, 3H), 8.02-8.14 (m, 6H), 6.8 (s, 3H), 5.11 (t, 7.5 Hz, 6H), 2.56 (t, J=7.5 Hz, 6H), 2.14 (m, 6H), 1.69 (m, 6H), 1.52 (m, 6H) ppm; ¹³C NMR (75 MHz, CD₃OD) δ 150.3, 148.9, 143.4, 139.4, 137.3, 132.2, 131.8, 131.4, 127.2, 123.1, 119.9, 59.4, 36.7, 32.3, 31.1, 27.3 ppm.

Example 22

Preparation of 1,3,5-tris-[5-(2-isoquinolinium)-pentyl]-benzene tribromide

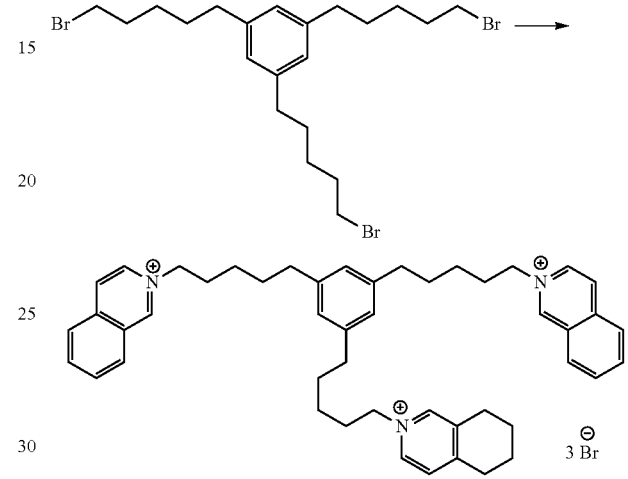

A mixture of 1,3,5-tris-(5-bromopentyl)-benzene (266 mg, 0.51 mmol) and quinoline (988 mg, 7.65 mmol) was heated at 60-70° C. for 12 hours. The resultant mixture was washed with diethyl ether and then dissolved in water (15 mL), the aqueous solution was washed with diethyl ether (30 mL×5), then lyophilized to afford 410 mg of 1,3,5-tris-[5-(2-isoquinolinium)-pentyl]-benzene tribromide. Yield 89%. ¹H NMR (300 MHz, CD₃OD) δ 9.99 (s, 3H), 8.69 (dd, J=6.9, 1.5 Hz, 3H), 8.47-8.54 (m, 6H), 8.22-8.36 (m, 6H), 8.07 (m, 3H), 4.78 (t, J=7.5 Hz, 6H), 2.53 (t, J=7.5 Hz, 6H), 2.15 (m, 6H), 1.67 (m, 6H), 1.44 (m, 6H); ¹³C NMR (75 MHz, CD₃OD) δ 150.8, 143.3, 138.8, 138.2, 135.8, 132.5, 131.5, 129.0, 128.5, 127.5, 127.1, 62.8, 36.5, 32.3, 32.0, 26.8 ppm.

Example 23

Preparation of 1,3,5-tris-[5-(3,5-lutidinium)-pentyl]-benzene tribromide

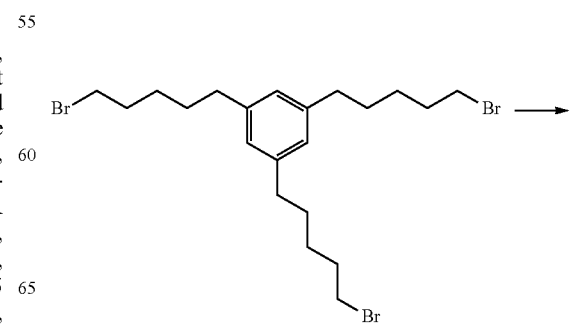

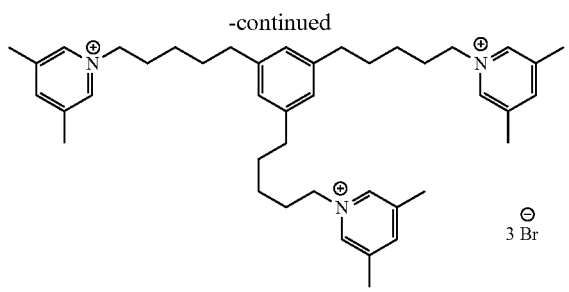

A mixture of 1,3,5-tris-(5-bromopentyl)-benzene (251 mg, 0.48 mmol) and 3,5-lutidine (770 mg, 7.20 mmol) was heated at 60-70° C. for 12 hours. The resultant mixture was washed with diethyl ether and then dissolved in water (15 mL), the aqueous solution was washed with diethyl ether (30 mL×3), then lyophilized to afford 372 mg of 1,3,5-tris-[5-(3,5-lutidinium)-pentyl]-benzene tribromide. Yield 92%. $^1$H NMR (300 MHz, CD$_3$OD) δ 8.75 (s, 6H), 8.26 (s, 3H), 6.84 (s, 3H), 4.56 (t, J=7.8 Hz, 6H), 2.58 (t, j=7.8 Hz, 6H), 2.54 (s, 18H), 2.05 (m, 6H), 1.69 (m, 6H), 1.43 (m, 6H) ppm; $^{13}$C NMR (75 MHz, CD$_3$OD) δ 147.7, 143.4, 142.7, 140.4, 127.2, 62.7, 36.7, 32.6, 32.3, 27.1, 18.5 ppm.

Example 24

Preparation of 1,3,5-tris-[5-(3,4-lutidinium)-pentyl]-benzene tribromide

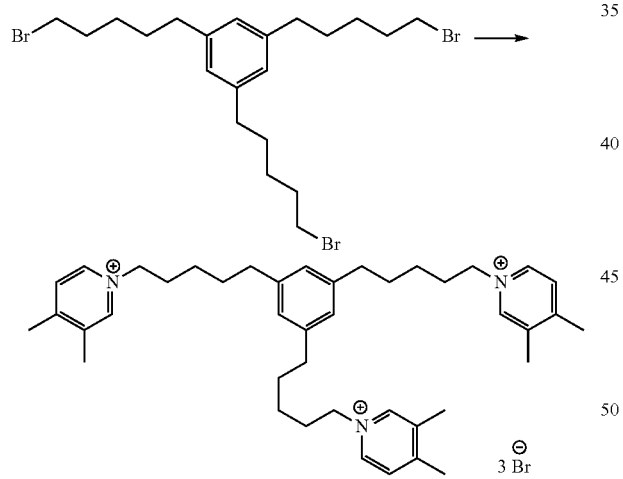

A mixture of 1,3,5-tris-(5-bromopentyl)-benzene (264 mg, 0.50 mmol) and 3,4-lutidine (808 mg, 7.50 mmol) was heated at 60-70° C. for 12 hours. The resultant mixture was washed with diethyl ether and then dissolved in water (15 mL), the aqueous solution was washed with diethyl ether (30 mL×3), then lyophilized to afford 370 mg of 1,3,5-tris-[5-(3,4-lutidinium)-pentyl]-benzene tribromide. Yield 87%. $^1$H NMR (300 MHz, CD$_3$OD) δ 8.78 (s, 3H), 8.67 (d, J=6.0 Hz, 3H), 7.85 (d, J=6.0 Hz, 3H), 6.83 (s, 3H), 4.53 (t, J=7.8 Hz, 6H), 2.59 (s, 9H), 2.57 (t, J=8.1 Hz, 6H), 2.48 (s, 9H), 2.03 (m, 6H), 1.68 (m, 6H), 1.42 (m, 6H) ppm; $^{13}$C NMR (75 MHz, CD$_3$OD) δ 159.8, 144.1, 143.4, 142.5, 139.9, 129.5, 127.2, 62.0, 36.7, 32A, 32.3, 27.0, 20.4, 17.1 ppm.

Example 25

Inhibition of [$^3$H]Nicotine (NIC) Binding Assay

Striata from two rats were dissected, pooled, and homogenized with a Tekmar polytron in 10 vol of ice-cold modified Krebs-HEPES buffer (20 mM HEPES, 118 mM NaCl, 4.8 mM KCl, 2.5 mM CaCl$_2$, 1.2 mM MgSO$_4$, adjusted to pH 7.5). The homogenates were incubated at 37° C. for 5 minutes and centrifuged at 15,000 g for 20 minutes. The pellet was resuspended in 10 volumes of ice-cold MilliQ water, incubated for 5 minutes at 37° C., and centrifuged at 15,000 g for 20 minutes. The second pellet was then resuspended in 10 volumes of fresh ice-cold 10% Krebs-HEPES buffer, incubated at 37° C., and centrifuged at 15,000 g for 20 minutes. The latter sequence of resuspension, incubation and centrifugation was repeated. The pellet was frozen under fresh 10% Krebs-HEPES buffer and stored at −40° C. until assay. Upon assay, the pellet was resuspended in Krebs-HEPES buffer, incubated at 37° C. for 5 minutes, and centrifuged at 15,000 g for 20 minutes. The final pellet was resuspended in 3.6 mL ice-cold MilliQ water which provided for approximately 200 µg protein per 100 µL aliquot. Competition assays were performed in duplicate in a final volume of 200 µl Krebs-HEPES buffer containing 250 mmol Tris buffer (pH 7.5 at 4° C.). Reactions were initiated by addition of 100 µL of membrane suspension to 3 nM [$^3$H]NIC (50 µL) and one of at least nine concentrations of analog (50 µL). After a 90 minute incubation at 4° C., reactions were terminated by dilution of the samples with 3 mL of ice-cold Krebs-HEPES buffer followed immediately by filtration through Whatman GF/B glass fiber filters (presoaked in 0.5% polyethyleneimine) using a Brandel Cell Harvester. Filters were rinsed three times with 3 mL of ice-cold Krebs-HEPES buffer, transferred to scintillation vials, and 5 mL scintillation cocktail (Research Products International Corp., Mt. Prospect, Ill.) added. Nonspecific binding determined in triplicate was defined as binding in the presence of 10 µM NIC. Binding parameters were determined using the weighted, least squares non-linear regression. The tris-quaternary ammonium salts were evaluated for their ability to displace [$^3$H]NIC binding from rat striatal membranes. The results are summarized in Table 1.

Example 26

Inhibition of [$^3$H]Methyllycaconitine (MLA) Binding Assay

Rat brain was dissected into the whole brain tissue without cortex, striatum and cerebellum and was frozen in liquid nitrogen and stored at −70° C. until use. The brain tissue was homogenized with a Tekmar Polytron (setting 40) in 20 volumes of ice-cold hypotonic buffer (2 mM HEPES, 14.4 mM NaCl, 0.15 mM KCl, 0.2 mM CaCl$_2$ and 0.1 mM MgSO$_4$, pH=7.5). The homogenate was incubated at 37° C. for 10 minutes and centrifuged at 25,000 g for 15 minutes at 40° C. The pellet was washed 3 times more by resuspension in 20 volumes of the same buffer and centrifugation at the above parameters. The final pellet was stored at −20° C. under 4.6 mL of the incubation buffer and was suspended just before the incubation with radioligand.

The binding of [$^3$H]MLA to probe α7-type neuronal nicotinic acetylcholine receptors was measured using a modification of the method of Davies et al., "Characterisation of the binding of [$^3$H]methyllycaconitine (MLA): a radioligand for labelling α7-type neuronal nicotinic acetylcholine receptors," Neuropharmacology, 38, 679-690 (1999). [$^3$H]MLA (25.4 Ci/mmol) was purchased from Tocris Cookson Ltd., Bristol, U.K. Binding was performed in duplicate, in a final volume of 250 μL of the incubation medium, containing 20 mM HEPES, 144 mM NaCl, 1.5 mM KCl, 2 mM $CaCl_2$, 1 mM $MgSO_4$ and 0.05% BSA, pH=7.5. Reaction was initiated by the addition of 100 μL of membrane suspension to the samples containing a desired concentration of test compounds and 2.5 mM [$^3$H]MLA (final concentration) and incubated for 2 hours at room temperature. Total binding was measured in the absence of unlabelled ligand, and nonspecific binding was determined by the presence of 1 μM unlabelled MLA. The binding reaction was terminated by dilution of samples with 3 mL of ice-cold incubation buffer followed by immediate filtration through glass fiber filters (S&S, grade #32, presoaked in 0.5% polyethylenimine) using a Brandel harvester system. Filters were rinsed three times with 3 mL of ice-cold buffer, transferred to scintillation vials and 4 mL of scintillation cocktail was added. Protein was measured using the Bradford dye-binding procedure with bovine serum albumin as the standard.

In order to determine if these compounds have selectivity at the α7 receptor subtype, the tris-alkyl pryidino analogs were evaluated for their ability to displace [$^3$H]MLA binding from rat brain membranes, as a result of their interaction with the α7 receptor (Table 1). In addition, the classical α7 receptor antagonist α-bungarotoxin was also examined in this assay for comparison. α-Bungarotoxin afforded a $K_1$ value of 28.6±5.4 nM in this assay. The tris-quaternary ammonium salts were evaluated for their ability to displace [$^3$H]MLA binding from rat brain membranes. The results are summarized in Table 1.

Example 27

Inhibition of Nicotine-Evoked [$^3$H]Neurotransmitter Release Assay

Rat striatal slices (500 μm thickness, 6-8 mg wet weight) were incubated for 30 minutes in Krebs buffer (118 mM NaCl, 4.7 mM KCl, 1.2 mM $MgCl_2$, 1.0 mM $NaH_2PO_4$, 1.3 mM $CaCl_2$, 11.1 mM glucose, 25 mM $NaHCO_3$, 0.11 mM: L-ascorbic acid and 0.004 mM disodium EDTA; pH 7.4, and saturated with 95% $O_2$/5% $CO_2$) in a metabolic shaker at 34° C. Slices were rinsed with 15 mL of fresh buffer and incubated for an additional 30 minutes in fresh buffer containing 0.1 μM [$^3$H]dopamine (DA; 6 slices/3 mL). Subsequently, slices were rinsed with 15 mL of fresh buffer and transferred to a glass superfusion chamber. Slices were superfused (1.0 mL/min) for 60 minutes with Krebs buffer containing nomifensine (10 μM) and pargyline (10 μM) and maintained at 34° C., pH 7.4 with continual aeration (95% $O_2$/5% $CO_2$). Two five minute samples (5 mL each) were collected to determine basal outflow of [$^3$H]DA. Analogs were added to the superfusion buffer after the collection of the second sample and remained in the buffer until 12 consecutive five minute samples were collected. Subsequently, S-(−)-nicotine (10 μM) was added to the buffer and an additional 12 consecutive five minute samples were collected. At the end of the experiment, each slice was solubilized and the [$^3$H] content of the tissue determined.

Radioactivity in the superfusate and tissue samples were determined by liquid scintillation spectroscopy. Fractional release for tritium collected in each sample was divided by the total tritium present at the time of sample collection and was expressed as a percentage of total tritium. Basal [$^3$H] outflow was calculated from the average of the tritium collected in the two five-minute samples just before addition of the analog. The sum of the increase in collected tritium resulting from either exposure to the test compound or exposure to S-(−)-nicotine in the absence and presence of the test compound equaled total [$^3$H] overflow. [$^3$H] Overflow was calculated by subtracting the [$^3$H] outflow during an equivalent period of prestimulation from the values in samples collected during and after drug exposure. Inasmuch as the radiolabelled compounds were not separated and identified, the tritium in the superfusate is referred to as either [$^3$H] outflow or [$^3$H] overflow, rather than [$^3$H]DA. [$^3$H] Overflow primarily represents [$^3$H]DA in the presence of nomifesine and pargyline in the superfusion buffer. The analogs were evaluated for their ability to evoke [$^3$H]DA release from rat striatal slices. In addition, the classical competitive nicotinic antagonist DHβE was also examined in this assay for comparison. None of the compounds examined had any significant [$^3$H]DA releasing properties in this assay in the concentration range tested.

Analogs were also evaluated for their ability to inhibit NIC evoked [$^3$H]DA release. In these experiments, the striatal slices were superfused for 60 minutes with 100 nM concentration of the analogs prior to NIC (10 μM) exposure. Antagonist activity was evaluated by comparing the NIC-evoked [$^3$H] overflow in the absence and presence of the analogs. The relative order of potency of the analogs for inhibition of NIC-evoked [$^3$H]DA release from rat striatal slices is illustrated in Table 1.

Example 28

Inhibition of ACh Evoked Current Through Expressed Nicotinic Receptors

Rat nicotinic receptor cDNAs clones were linearized and purified, and RNA transcripts were prepared in vitro using the appropriate mMessage mMachine kit. Mature (>9 cm) female *Xenopus laevis* African toads (Nasco, Ft. Atkinson, Wis.), housed in the Division of Lab Animal Resources at the University of Florida were used as a source of oocytes. Prior to surgery, frogs were anesthetized by placing the animal in a 1.5 g/L solution of MS222 for 30 minutes. Oocytes were removed from an incision made in the abdomen. In order to remove the follicular cell layer, harvested oocytes were treated with 1.25 mg/mL collagenase for 2 hours at room temperature in calcium-free Barth's solution (88 mM NaCl, 1 mM KCl, 2.38 mM $NaHCO_3$, 0.82 mM $MgSO_4$, 15 mM HEPES, pH 7.6, 0.1 mg/mL gentamicin sulfate). Subsequently, stage 5 oocytes were isolated and injected with 5-20 ng in 50 mL each of the appropriate subunit cRNAs. Recordings were made 2 to 15 days after injection.

Electrophysiology experiments were conducted using OpusXpress 6000A (Axon instruments, Union City, Calif.), or manual oocyte two-electrode voltage-clamp systems as previously reported (Stokes et al., 2004). OpusXpress is an integrated system that provides automated impalement and voltage clamp of up to eight oocytes in parallel. Cells were automatically perfused with bath solution, and agonist solutions were delivered from a 96-well plate. Both the voltage and current electrodes were filled with 3 M KCl. The agonist solutions were applied via disposable tips, which eliminated the possibility of cross-contamination. Fresh ACh stock solutions were made daily in Ringer's solution and diluted. Flow rates were set at 2 mL/min for experiments with α7 nicotinic receptors and 4 mL/min for other nicotinic receptor subtypes. Cells were voltage-clamped at a holding potential of −60 mV. Data were collected at 50 Hz and filtered at 20 Hz. ACh applications were 12 seconds in duration followed by 181 second washout periods with α7 nicotinic receptors and 8 seconds with 241 second wash periods for other nicotinic receptor subtypes. For manual oocyte recordings, Warner Instruments (Hamden, Conn.) OC-725C oocyte aplifiers were used, and data were acquired with a minidigi or digidata 1200A with pClamp9 software (Axon instruments). Sampling rates were between 10 and 20 HZ and the data were filtered at 6 Hz. Cells were voltage clamped at a holding potential of −50 mV.

Each oocyte received two initial control applications of ACh, then a nicotine or analog application, and then a follow-up control application of ACh. The control ACh concentrations for α7 and α4β2 receptors were 300 µM and 10 µM each, respectively, and 100 µM for the other subtype combinations tested. Responses to each nicotine or analog application were calculated relative to the preceding ACh control responses in order to normalize the data, compensating for the varying levels of channel expression among the oocytes. Responses to nicotine or analog were initially normalized to the ACh control response values and then adjusted to reflect drug response relative to ACh maximums. Responses for α7 receptors were calculated as net charge (Papke et al., 2002). For subtypes other than α7, responses were calculated from the peak current amplitudes. Means and standard errors (SEM) were calculated from the normalized responses of at least four oocytes for each drug concentration. Since the application of some concentrations of nicotine caused the subsequent ACh control responses to be reduced due to some form of residual inhibition (or prolonged desensitization), subsequent control responses were compared to the pre-application control ACh responses. When cells failed to recover to at least 75% of the previous control they were replaced with new cells.

For concentration-response relations, data derived from net-charge analyses were plotted using Kaleidagraph 3.0.2 (Abelbeck Software; Reading, Pa.) and curves were generated from the Hill equation $$\text{Response} = \frac{I_{max}[\text{agonist}]^n}{[\text{agonist}]^n + (EC_{50})^n}$$

where $I_{max}$ denotes the maximal response for a particular agonist/subunit combination, and represents the Hill coefficient. $I_{max}$, n and the $EC_{50}$ were all unconstrained for the fitting of the nicotine responses, and $I_{max}$ was constrained to equal 1 for the ACh responses, since we used the maximal ACh responses to define full agonist activity. Negative Hill slopes were applied for the calculation of $IC_{50}$ values associated with residual inhibition or desensitization when observed.

Results from these experiments are shown in FIGS. 1-4.

FIG. 1 shows concentration-response curves for GZ551A in each of four subtypes of nicotinic receptor (α4β2, α3β2, α3β4 and α7) expressed in Xenopus oocytes. Data are expressed as mean±standard error of the mean and the X-axis illustrates mM concentration of analog. The electrophysiological response to the analog during co-application of acetylcholine is normalized to the acetylcholine control response obtained for each oocyte. As such, 1.0 indicates that the electrophysiological response to the analog plus acetylcholine was not different from the response to acetylcholine alone (control), i.e., 100% response. Normalization provides compensation for the varying levels of nicotinic receptor expression among the oocytes. Concentration of analog which inhibits the response to acetylcholine by 50% (IC50 value) are provided in the legend for each nicotinic receptor subtype. Generally, GZ551A was a potent and selective inhibitor of the α7 nicotinic receptor subtype.

Figure 2:
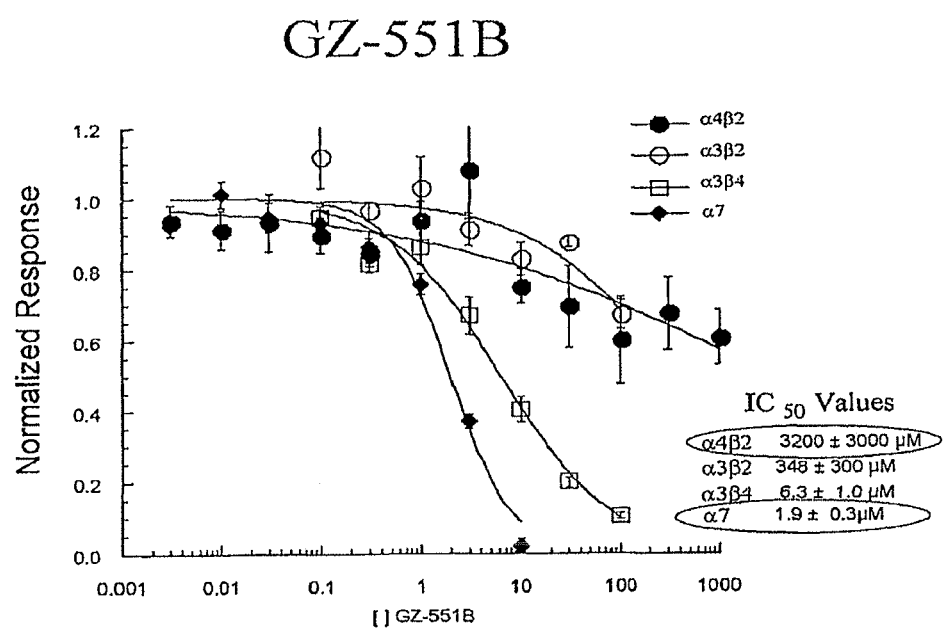
FIG. 2 shows concentration-response curves for GZ551B in each four subtypes of nicotinic receptor ($\alpha 4\beta 2$, $\alpha 3\beta 2$, $\alpha 3\beta 4$ and $\alpha 7$) expressed in *Xenopus* oocytes.

FIG. 2 shows concentration-response curves for GZ55113 in each of four subtypes of nicotinic receptor (α4β2, α3β2, α3β4 and α7) expressed in Xenopus oocytes. Data are expressed as mean standard error of the mean and the X-axis illustrates mM concentration of analog. The electrophysiological response to the analog during co-application of acetylcholine is normalized to the acetylcholine control response obtained for each oocyte. As such, 1.0 indicates that the electrophysiological response to the analog plus acetylcholine was not different from the response to acetylcholine alone (control), i.e., 100% response. Normalization provides compensation for the varying levels of nicotinic receptor expression among the oocytes. Concentration of analog which inhibits the response to acetylcholine by 50% (IC50 value) are provided in the legend for each nicotinic receptor subtype. Generally, GZ551B was most potent as an inhibitor of the α7 nicotinic receptor subtype, but was not selective, since it also potently inhibited the α3β4 nicotinic receptor subtype.

Figure 3:
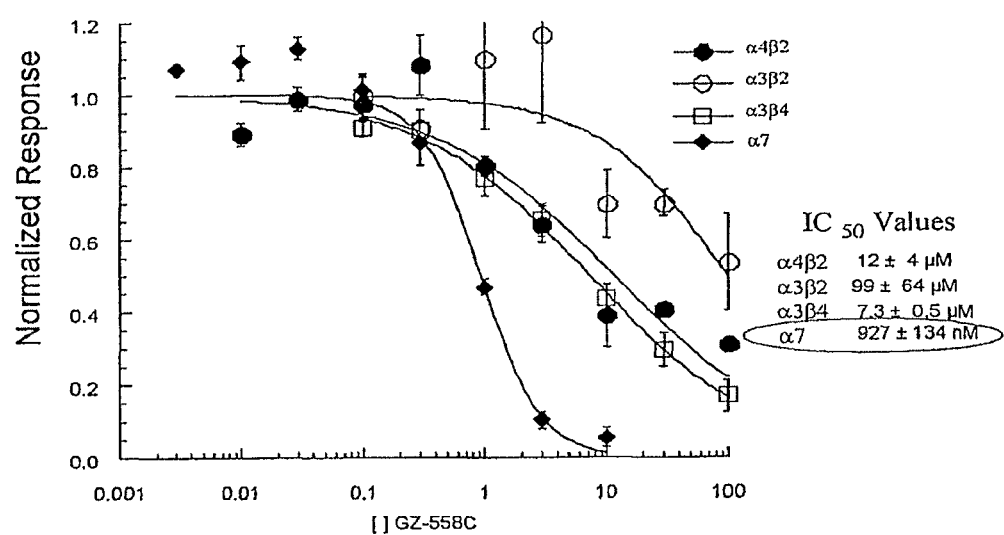
FIG. 3 shows concentration-response curves for GZ558C in each four subtypes of nicotinic receptor ($\alpha 4\beta 2$, $\alpha 3\beta 2$, $\alpha 3\beta 4$ and $\alpha 7$) expressed in *Xenopus* oocytes.

FIG. 3 shows concentration-response curves for GZ558C in each four subtypes of nicotinic receptor (α4β2, α3β2, α3β4 and α7) expressed in Xenopus oocytes. Data are expressed as mean±standard error of the mean and the X-axis illustrates mM concentration of analog. The electrophysiological response to the analog during co-application of acetylcholine is normalized to the acetylcholine control response obtained for each oocyte. As such, 1.0 indicates that the electrophysiological response to the analog plus acetylcholine was not different from the response to acetylcholine alone (control), i.e., 100% response. Normalization provides compensation for the varying levels of nicotinic receptor expression among the oocytes. Concentration of analog which inhibits the response to acetylcholine by 50% (IC50 value) are provided in the legend for each nicotinic receptor subtype. Generally, GZ558C was also a potent and selective inhibitor of the α7 nicotinic receptor subtype.

Figure 4:
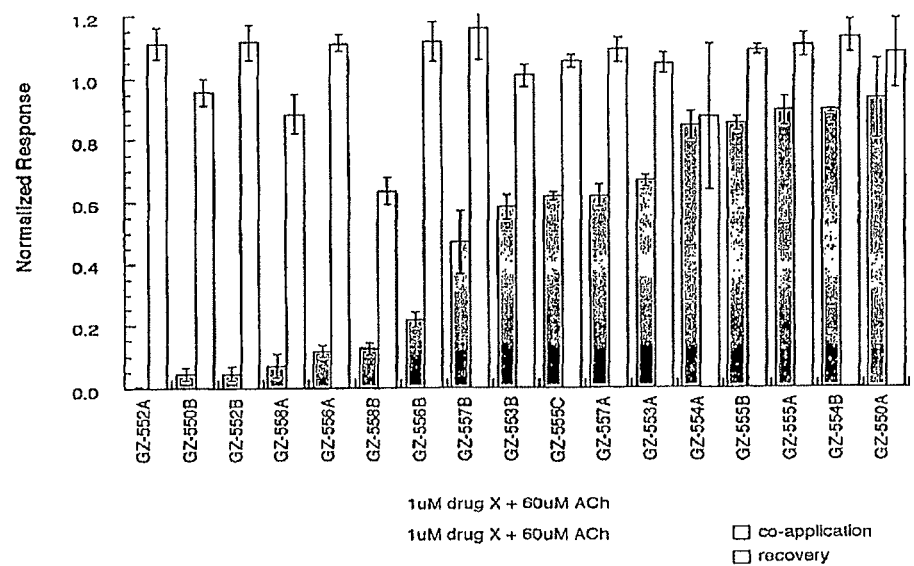
FIG. 4 shows the inhibitory response of the $\alpha 7$ nicotinic receptor subtype expressed in *Xenopus* oocytes to 1.0 mM analog concentration for 17 analogs co-applied with 60 mM acetylcholine (filled bars), as well as recovery from analog-induced inhibition following washing of the preparation (open bars).

FIG. 4 shows the inhibitory response of the α7 nicotinic receptor subtype expressed in Xenopus oocytes to 1.0 mM analog concentration for 17 analogs co-applied with 60 mM acetylcholine (filled bars), as well as recovery from analog-induced inhibition following washing of the preparation (open bars). Data are expressed as mean±standard error of the mean response for each analog. The electrophysiological response to the analog during co-application of acetylcholine is normalized to the acetylcholine control response obtained for each oocyte. As such, 1.0 indicates that the electrophysiological response to the analog plus acetylcholine was not different from the response to acetylcholine alone (control), i.e., 100% response or no inhibitory activity. Normalization provides compensation for the varying levels of nicotinic receptor expression among the oocytes. Generally, the figure shows that structural variation in the analog series has a profound effect with regards to inhibition of the α7 nicotinic receptor subtype. Furthermore, recovery was not complete for one analog, GZ558B.

TABLE 1
tris-Quaternary Ammonium Salts Inhibition of [³H]NIC and [³H]MLA Binding to Rat Striatal Nicotinic Receptors
| Compound | Inhibition of [³H]Nicotine binding | Inhibition of [³H]MLA binding | Inhibition of Nicotine-evoked [³H]DA Release |
|---|---|---|---|
| GZ-550A | 10 ± 1.9% | 0 ± 0% | 46% |
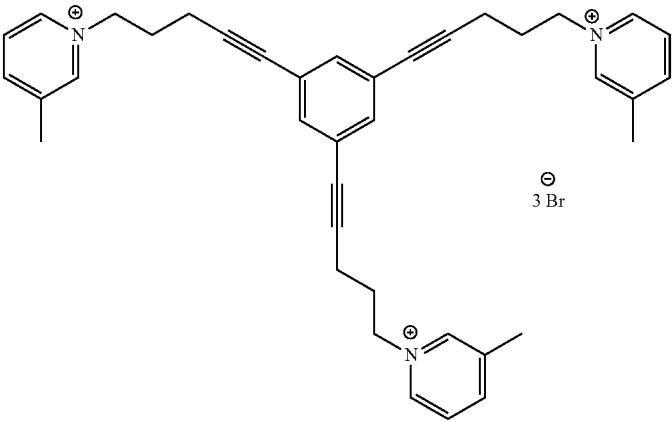 [SMILES: Cc1ccc[n+](CCCC#Cc2cc(C#CCCC[n+]3cccc(C)c3)cc(C#CCCC[n+]3cccc(C)c3)c2)c1]
| | | | |
|---|---|---|---|
| GZ-550B | 15 ± 0.9% | 39 ± 2.2% | 49% |
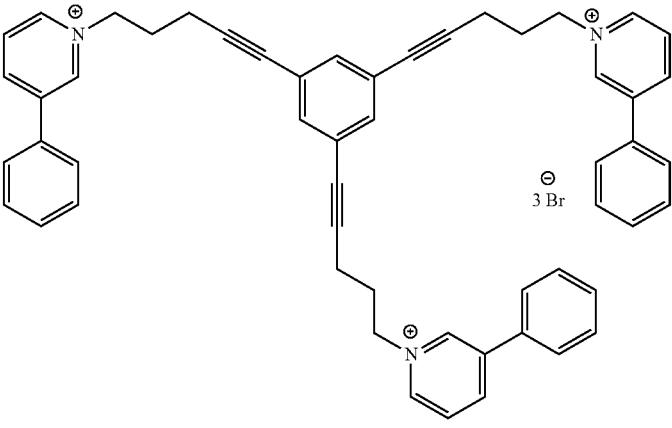 [SMILES: C(#Cc1cc(C#CCCC[n+]2cccc(-c3ccccc3)c2)cc(C#CCCC[n+]2cccc(-c3ccccc3)c2)c1)CCC[n+]1cccc(-c2ccccc2)c1]
| | | | |
|---|---|---|---|
| GZ-551A | 6.80 ± 2.0% | 30 ± 2.0% | 52% |
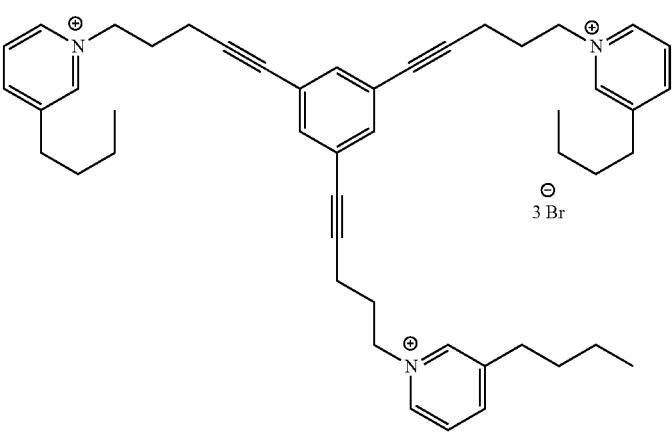 [SMILES: CCCCc1ccc[n+](CCCC#Cc2cc(C#CCCC[n+]3cccc(CCCC)c3)cc(C#CCCC[n+]3cccc(CCCC)c3)c2)c1]

TABLE 1-continued tris-Quaternary Ammonium Salts Inhibition of [$^3$H]NIC and [$^3$H]MLA Binding to Rat Striatal Nicotinic Receptors

| Compound | Inhibition of [$^3$H]Nicotine binding | Inhibition of [$^3$H]MLA binding | Inhibition of Nicotine-evoked [$^3$H]DA Release |
|---|---|---|---|
| GZ-551B | 44 ± 3.1% | 4.2 ± 2.2% | 63% |
| GZ-552A | 7.0 ± 3.8% | 21 ± 6.0% | 72% |
| GZ-552B | 9.2 ± 5.0% | 4.5 ± 2.6% | 49% |

TABLE 1-continued tris-Quaternary Ammonium Salts Inhibition of [³H]NIC and [³H]MLA Binding to Rat Striatal Nicotinic Receptors

| Compound | Inhibition of [³H]Nicotine binding | Inhibition of [³H]MLA binding | Inhibition of Nicotine-evoked [³H]DA Release |
|---|---|---|---|
| GZ-553A | 8.9 ± 2.9% | 0 ± 0% | 31% |
| GZ-553B | 4.0 ± 1.4% | 1.8 ± 1.8% | 0% |
| GZ-554A | 4.5 ± 2.0% | 0 ± 0% | 68% |

TABLE 1-continued tris-Quaternary Ammonium Salts Inhibition of [³H]NIC and [³H]MLA Binding to Rat Striatal Nicotinic Receptors

| Compound | Inhibition of [³H]Nicotine binding | Inhibition of [³H]MLA binding | Inhibition of Nicotine-evoked [³H]DA Release |
|---|---|---|---|
| GZ-554B | 21 ± 4.5% | 0 ± 0% | 34% |

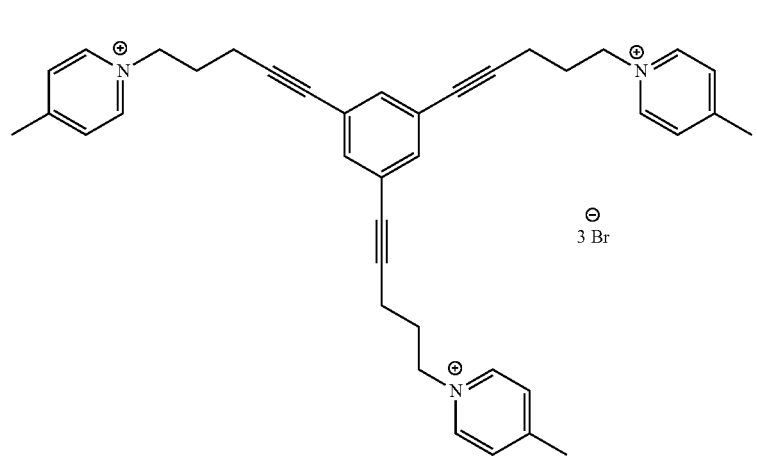

| Compound | Inhibition of [³H]Nicotine binding | Inhibition of [³H]MLA binding | Inhibition of Nicotine-evoked [³H]DA Release |
|---|---|---|---|
| GZ-555A | 14 ± 6.1% | 1.2 ± 1.2% | 42% |

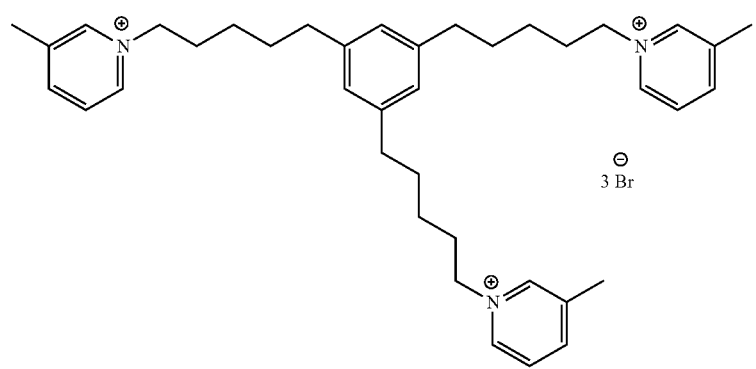

TABLE 1-continued
tris-Quaternary Ammonium Salts Inhibition of [³H]NIC and [³H]MLA Binding to Rat Striatal Nicotinic Receptors
| Compound | Inhibition of [³H]Nicotine binding | Inhibition of [³H]MLA binding | Inhibition of Nicotine-evoked [³H]DA Release |
|---|---|---|---|
| GZ-555B | 8.6 ± 7.2% | 0 ± 0% | 25% |
| GZ-555C | 6.0 ± 3.4% | 0 ± 0% | 37 ± 17% (n = 4) |
| GZ-556A | 5.7 ± 5.7% | 6.8 ± 0.9% | 8.0 ± 6.4% (n = 3) |
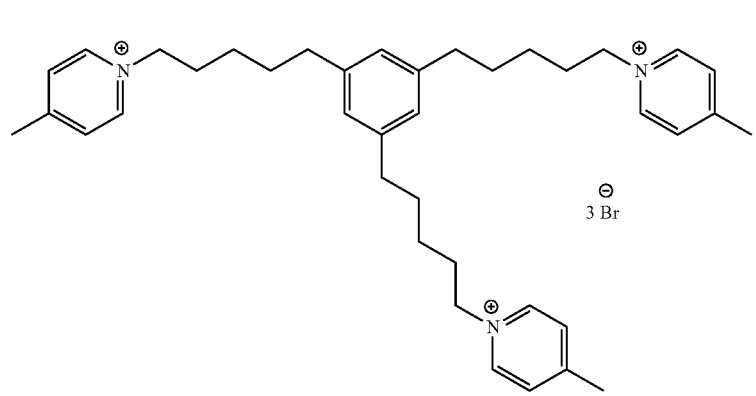

TABLE 1-continued tris-Quaternary Ammonium Salts Inhibition of [$^3$H]NIC and [$^3$H]MLA Binding to Rat Striatal Nicotinic Receptors

| Compound | Inhibition of [$^3$H]Nicotine binding | Inhibition of [$^3$H]MLA binding | Inhibition of Nicotine-evoked [$^3$H]DA Release |
|---|---|---|---|
| GZ-556B | 8.4 ± 7.6% | 2.5 ± 1.5% | 28 ± 11% (n = 3) |
| GZ-557A | 11 ± 2.9% | 6.5 ± 3.6% | 39 ± 18% (n = 5) |
| GZ-557B | 9.3 ± 4.1% | 0.2 ± 0.2% | 50 ± 21% (n = 5) |

TABLE 1-continued
tris-Quaternary Ammonium Salts Inhibition of [³H]NIC and [³H]MLA Binding to Rat Striatal Nicotinic Receptors
| Compound | Inhibition of [³H]Nicotine binding | Inhibition of [³H]MLA binding | Inhibition of Nicotine-evoked [³H]DA Release |
|---|---|---|---|
| GZ-558A | 14 ± 5.8% | 19 ± 1.7% | 6.0 ± 5.0% (n = 3) |
| 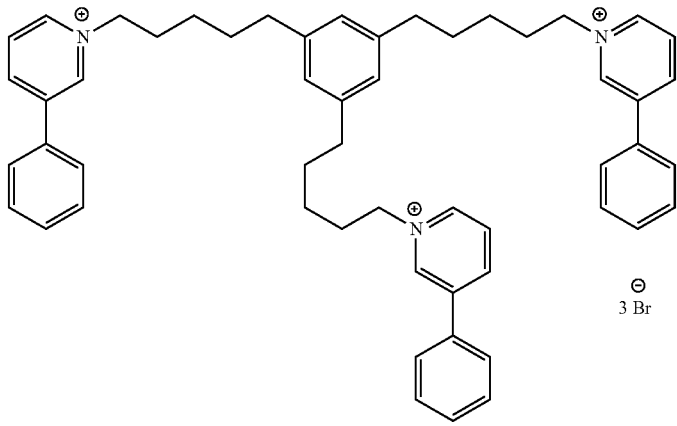 [SMILES: c1ccc(-c2ccc[n+](CCCCCc3cc(CCCCC[n+]4cccc(-c5ccccc5)c4)cc(CCCCC[n+]4cccc(-c5ccccc5)c4)c3)c2)cc1] | | | |
| GZ-558B | 6.2 ± 4.0% | 4.4 ± 3.3% | 68 ± 14% (n = 4) |
| 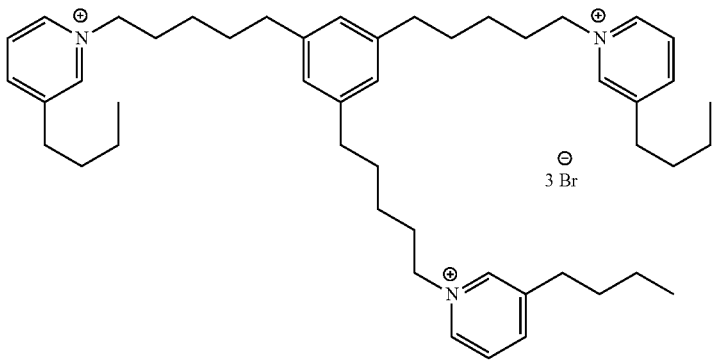 [SMILES: CCCCc1ccc[n+](CCCCCc2cc(CCCCC[n+]3cccc(CCCC)c3)cc(CCCCC[n+]3cccc(CCCC)c3)c2)c1] | | | |
| GZ-558C | 81 ± 2.3% | 7.9 ± 7.1% | 35% |
| 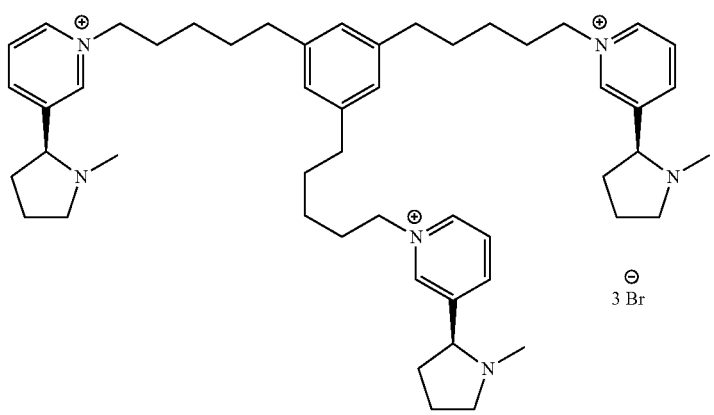 [SMILES: CN1CCC[C@H]1c1ccc[n+](CCCCCc2cc(CCCCC[n+]3cccc([C@@H]4CCCN4C)c3)cc(CCCCC[n+]3cccc([C@@H]4CCCN4C)c3)c2)c1] | | | |

Data are % inhibition at 100 nM concentration of analog for at least 1-3 independent experiments. Specific binding in the [$^3$H]NIC binding assay is calculated at the difference between the total binding of 3 nM [$^3$H]NIC and nonspecific binding in the presence of 10 μM cold nicotine. Specific binding for the [$^3$H]MLA binding assay is calculated as the difference between the total binding of 2.5 nM [$^3$H]MLA to the receptors alone and its nonspecific binding in the presence of 1 μM cold MLA. Analog-induced inhibition of nicotine-evoked [$^3$H]DA release is calculated as a percent of that in the absence of analog.

It will be appreciated that, although specific embodiments of the invention have been described herein for purposes of illustration, various modifications may be made without departing from the spirit and scope of the invention. All such modifications and variations are intended to be included herein within the scope of this disclosure and the present invention and protected by the following claims.

We claim:

1. A method for selectively modulating the function of a nicotinic acetylcholine receptor comprising administering to a mammalian subject in need thereof a therapeutically effective amount of a compound of Formula (I):

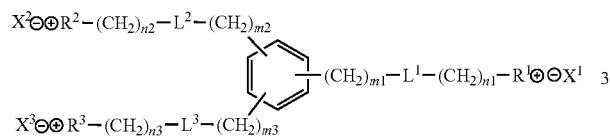
(I)

wherein the three side chains attached to the phenyl ring may be connected to the 1, 2, and 3 positions; the 1, 2, and 4 positions; or the 1, 3 and 5 positions of the phenyl ring;

wherein m1, m2 and m3 are each independently 0, 1, 2, 3, 4 or 5;

wherein n1, n2, and n3 are each independently 1, 2, 3, 4, or 5;

wherein $X^{1\ominus}$, $X^{2\ominus}$, and $X^{3\ominus}$ are each independently an organic or inorganic anion;

wherein $L^1$, $L^2$ and $L^3$ are each independently chosen from the group consisting of —CH$_2$—CH$_2$—, cis —CH=CH—, trans —CH=CH—, —C≡C—, —CH$_2$—S—, —S—CH$_2$—, —Se—CH$_2$—, —CH$_2$—Se—, —CH$_2$—O—, —O—CH$_2$—, —CH$_2$—NH—, —NH—CH$_2$—, —CH$_2$—NR— where R is a branched or straight chain alkyl group of one to four carbons, —NR—CH$_2$— where R is a branched or straight chain alkyl group of one to four carbons, —CH=N—, —N=CH—, and —N=N—;

wherein $R^1$, $R^2$, and $R^3$ are each independently five or six membered nitrogen containing rings as shown in formulas (IIA) and (IIB)

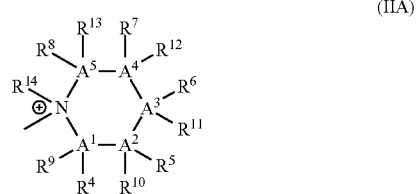
(IIA)

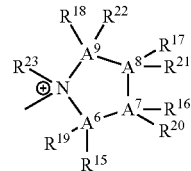
(IIB)

wherein $A^1$ is carbon or nitrogen, provided that when $A^1$ joins a ring atom with an unsaturated bond or is a nitrogen, $R^9$ is absent, and when $A^1$ joins a ring atom with an unsaturated bond and is a nitrogen, both $R^4$ and $R^9$ are absent;

wherein $A^2$ is carbon or nitrogen, provided that when $A^2$ joins a ring atom with an unsaturated bond or is a nitrogen, $R^{10}$ is absent, and when $A^2$ joins a ring atom with an unsaturated bond and is a nitrogen, both $R^5$ and $R^{10}$ are absent;

wherein $A^3$ is carbon or nitrogen, provided that when $A^3$ joins a ring atom with an unsaturated bond or is a nitrogen, $R^{11}$ is absent, and when $A^3$ joins a ring atom with an unsaturated bond and is a nitrogen, both $R^6$ and $R^{11}$ are absent;

wherein $A^4$ is carbon or nitrogen, provided that when $A^4$ joins a ring atom with an unsaturated bond or is a nitrogen, $R^{12}$ is absent, and when $A^4$ joins a ring atom with an unsaturated bond and is a nitrogen, both $R^7$ and $R^{12}$ are absent;

wherein $A^5$ is carbon or nitrogen, provided that when $A^5$ joins a ring atom with an unsaturated bond or is a nitrogen, $R^{13}$ is absent, and when $A^5$ joins a ring atom with an unsaturated bond and is a nitrogen, both $R^8$ and $R^{13}$ are absent;

wherein $A^6$ is carbon or nitrogen, provided that when $A^6$ joins a ring atom with an unsaturated bond or is a nitrogen, $R^{19}$ is absent, and when $A^6$ joins a ring atom with an unsaturated bond and is a nitrogen, both $R^{15}$ and $R^{19}$ are absent;

wherein $A^7$ is carbon or nitrogen, provided that when $A^7$ joins a ring atom with an unsaturated bond or is a nitrogen, $R^{20}$ is absent, and when $A^7$ joins a ring atom with an unsaturated bond and is a nitrogen, both $R^{16}$ and $R^{20}$ are absent;

wherein $A^8$ is carbon or nitrogen, provided that when $A^8$ joins a ring atom with an unsaturated bond or is a nitrogen, $R^{21}$ is absent, and when $A^8$ joins a ring atom with an unsaturated bond and is a nitrogen, both $R^{17}$ and $R^{21}$ are absent;

wherein $A^9$ is carbon or nitrogen, provided that when $A^9$ joins a ring atom with an unsaturated bond or is a nitrogen, $R^{22}$ is absent, and when $A^9$ joins a ring atom with an unsaturated bond and is a nitrogen, both $R^{18}$ and $R^{22}$ are absent;

wherein $R^{14}$ or $R^{23}$ is absent when any of the bonds to the ammonium nitrogen is unsaturated, and $R^{14}$ or $R^{23}$ is a straight chain or branched alkyl group of four carbons or fewer when all of the bonds to the ammonium nitrogen are saturated;

wherein $R^4$, $R^5$, $R^6$, $R^7$, $R^8$, $R^9$, $R^{10}$, $R^{11}$, $R^{12}$, and $R^{13}$ or $R^{15}$, $R^{16}$, $R^{17}$, $R^{18}$, $R^{19}$, $R^{20}$, $R^{21}$, and $R^{22}$, when present, are each independently selected from hydrogen; alkyl; substituted alkyl; cycloalkyl; substituted cycloalkyl; alkenyl; substituted alkenyl; alkynyl; substituted alkynyl; aryl; substituted aryl; alkylaryl; substituted alkylaryl; arylalkyl; substituted arylalkyl; arylalkenyl; substituted arylalkenyl; arylalkynyl; substituted arylalkynyl; heterocyclic; substituted heterocyclic; halo; cyano; nitro; $SOY^1$, $SO_2Y^1$, $SO_2OY^1$ or $SO_2NHY^1$, where $Y^1$ is selected from hydrogen, lower alkyl, alkenyl, alkynyl or aryl, and where $Y^1$ is not hydrogen in $SOY^1$ and if $Y^1$ is alkenyl or alkynyl, the site of unsaturation is not conjugated with a heteroatom; $COY^2$, where $Y^2$ is selected from hydrogen, alkyl, substituted alkyl, cycloalkyl, substituted cycloalkyl, alkoxy, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, heterocyclic, or substituted heterocyclic, and where if $Y^2$ comprises alkenyl or alkynyl, the site of unsaturation is not conjugated with the carbonyl group; $OY^3$, where $Y^3$ is selected from hydrogen, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, acyl, susbstituted acyl, alkylsulfonyl, arylsulfonyl, heterocyclic, or substituted heterocyclic, where if $Y^3$ comprises alkenyl or alkynyl, the site of unsaturation is not conjugated with the oxygen; $NY^4Y^5$, where $Y^4$ and $Y^5$ are each independently selected from hydrogen, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, acyl, susbstituted acyl, alkylsulfonyl, arylsulfonyl, heterocyclic, or substituted heterocyclic, where if $Y^4$ or $Y^5$ comprises alkenyl or alkynyl, the site of unsaturation is not conjugated with the nitrogen; $SY^6$, where $Y^6$ is selected from hydrogen, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, heterocyclic, or substituted heterocyclic, and where if $Y^6$ comprises alkenyl or alkynyl, the site of unsaturation is not conjugated with the sulfur; or $R^4$ and $R^5$ together with $A^1$ and $A^2$, or $R^5$ and $R^6$ together with $A^2$ and $A^3$, or $R^{15}$ and $R^{16}$ together with $A^6$ and $A^7$, or $R^{16}$ and $R^{17}$ together with $A^7$ and $A^8$ independently form a three to eight member cyclolkane, substituted cycloalkane, cycloalkene, substituted cycloalkene, aryl, substituted aryl, heterocycle with one to three hetero atoms in the ring, or substituted heterocycle with one to three hetero atoms in the ring.

2. The method of claim 1, wherein the compound of Formula (I) binds selectively to one or more subtypes of the nicotinic acetylcholine receptors.

3. The method of claim 2, wherein the selective modulation comprises activation of the function of nicotinic acetylcholine receptors as an agonist or as a partial agonist.

4. The method of claim 2, wherein the selective modulation comprises inactivation of the function of nicotinic acetylcholine receptors as an antagonist.

5. The method of claim 2, wherein there is a decrease in the stimulant-evoked release of a neurotransmitter from a central nervous system tissue.

6. The method of claim 2, wherein there is an increase in the release of a neurotransmitter from a central nervous system tissue.

7. The method of claim 5, wherein the neurotransmitter released is selected from the group consisting of dopamine, norepinephrine, serotonin, gamma-aminobutyric acid, and glutamate.

8. The method of claim 6, wherein the neurotransmitter released is selected from the group consisting of dopamine, norepinephrine, serotonin, gamma-aminobutyric acid, and glutamate.

9. The method of claim 1, wherein the compound of Formula (I) is selected from the group consisting of:
   1,3,5-tris-[5-(2-picolinium)-pent-1-ynyl]-benzene tribromide;
   1,3,5-tris-[5-(3-picolinium)-pent-1-ynyl]-benzene tribromide;
   1,3,5-tris-[5-(4-picolinium)-pent-1-ynyl]-benzene tribromide;
   1,3,5-tris-[5-(3-butyl-pyridinium)-pent-1-ynyl]-benzene tribromide;
   1,3,5-tris-[5-(3-phenyl-pyridinium)-pent-1-ynyl]-benzene tribromide;
   1,3,5-tris-{5-[3-(1-methyl-2-S-pyrrolidinyl)pyridinium]-pent-1-ynyl}-benzene tribromide;
   1,3,5-tris-[5-(1-quinolinium)-pent-1-ynyl]-benzene tribromide;
   1,3,5-tris-[5-(2-isoquinolinium)-pent-1-ynyl]-benzene tribromide;
   1,3,5-tris-[5-(3,5-lutidinium)-pent-1-ynyl]-benzene tribromide;
   1,3,5-tris-[5-(3,4-lutidinium)-pent-1-ynyl]-benzene tribromide;
   1,3,5-tris-[5-(2-picolinium)-pentyl]-benzene tribromide;
   1,3,5-tris-[5-(3-picolinium)-pentyl]-benzene tribromide;
   1,3,5-tris-[5-(4-picolinium)-pentyl]-benzene tribromide;
   1,3,5-tris-[5-(3-butyl-pyridinium)-pentyl]-benzene tribromide;
   1,3,5-tris-[5-(3-phenyl-pyridinium)-pentyl]-benzene tribromide;
   1,3,5-tris-{5-[3-(1-methyl-2-S-pyrrolidinyl) pyridinium]-pentyl}-benzene tribromide;
   1,3,5-tris-[5-(1-quinolinium)-pentyl]-benzene tribromide;
   1,3,5-tris-[5-(2-isoquinolinium)-pentyl]-benzene tribromide;
   1,3,5-tris-[5-(3,5-lutidinium)-pentyl]-benzene tribromide; and
   1,3,5-tris-[5-(3,4-lutidinium)-pentyl]-benzene tribromide.

* * * * *